US006455314B1

(12) United States Patent
Wickham et al.

(10) Patent No.: US 6,455,314 B1
(45) Date of Patent: Sep. 24, 2002

(54) ALTERNATIVELY TARGETED ADENOVIRUS

(75) Inventors: Thomas J. Wickham, Falls Church, VA (US); Imre Kovesdi, Rockville, MD (US); Petrus W. Roelvink, Olney, MD (US); Joseph T. Bruder, Ijamsville, MD (US)

(73) Assignee: GenVec, Inc., Gaithersburg, MD (US)

( * ) Notice: Subject to any disclaimer, the term of this patent is extended or adjusted under 35 U.S.C. 154(b) by 0 days.

(21) Appl. No.: 09/393,627

(22) Filed: Sep. 10, 1999

Related U.S. Application Data

(60) Provisional application No. 60/099,851, filed on Sep. 11, 1998, and provisional application No. 60/136,529, filed on May 28, 1999.

(51) Int. Cl.[7] .................... C12N 15/86; C12N 15/861; C12N 15/09; C07H 21/04
(52) U.S. Cl. ................. 435/456; 435/235.1; 435/320.1; 435/325; 435/69.7; 435/69.1; 530/350; 530/300; 530/402; 536/23.1; 536/23.4; 536/24.1
(58) Field of Search .......................... 530/300, 350, 530/402; 435/69.1, 320.1, 235.1, 69.7, 456, 325; 536/23.1, 23.4, 24.1

(56) References Cited

U.S. PATENT DOCUMENTS

| | | |
|---|---|---|
| 4,578,079 A | 3/1986 | Ruoslahti et al. |
| 4,593,002 A | 6/1986 | Dulbecco |
| 4,792,525 A | 12/1988 | Ruoslahti et al. |
| 5,166,320 A | 11/1992 | Wu et al. |
| 5,223,409 A | 6/1993 | Ladner et al. |
| 5,403,484 A | 4/1995 | Ladner et al. |
| 5,443,953 A | 8/1995 | Hansen et al. |
| 5,521,291 A | 5/1996 | Curiel et al. |
| 5,543,328 A | 8/1996 | McClelland et al. |
| 5,547,932 A | 8/1996 | Curiel et al. |
| 5,559,099 A | 9/1996 | Wickham et al. |
| 5,571,698 A | 11/1996 | Ladner et al. |
| 5,622,699 A | 4/1997 | Ruoslahti et al. |
| 5,663,143 A | 9/1997 | Ley et al. |
| 5,693,509 A | 12/1997 | Cotten et al. |
| 5,695,991 A | 12/1997 | Lindholm et al. |
| 5,712,136 A | 1/1998 | Wickham et al. |
| 5,731,190 A | 3/1998 | Wickham et al. |
| 5,756,086 A | 5/1998 | McClelland et al. |
| 5,770,442 A | 6/1998 | Wickham et al. |
| 5,837,500 A | 11/1998 | Ladner et al. |
| 5,871,727 A | 2/1999 | Curiel |
| 5,885,808 A | 3/1999 | Spooner et al. |
| 5,922,315 A | 7/1999 | Roy |
| 5,981,273 A | 11/1999 | Curiel et al. |

FOREIGN PATENT DOCUMENTS

| | | |
|---|---|---|
| EP | 846772 | 6/1998 |
| EP | 959135 | 11/1999 |
| EP | 959136 | 11/1999 |
| EP | 960942 | 12/1999 |
| JP | 2-078631 | 3/1990 |
| WO | WO 93/07282 | 3/1990 |
| WO | WO 93/07283 | 4/1993 |
| WO | WO 94/10323 | 5/1994 |
| WO | WO 94/15644 | 7/1994 |
| WO | WO 94/17832 | 8/1994 |
| WO | WO 94/24299 | 10/1994 |
| WO | WO 95/05201 | 2/1995 |
| WO | WO 95/26412 | 10/1995 |
| WO | WO 96/07734 | 3/1996 |
| WO | WO 96/13597 | 5/1996 |
| WO | WO 95/31566 | 11/1996 |
| WO | WO 97/06826 | 2/1997 |
| WO | WO 97/24453 | 7/1997 |
| WO | WO 97/38723 | 10/1997 |
| WO | WO 98/13499 | 4/1998 |
| WO | WO 98/22609 | 5/1998 |
| WO | WO 98/32842 | 7/1998 |
| WO | WO 98/33929 | 7/1998 |
| WO | WO 98/39464 | 9/1998 |
| WO | WO 98/44121 | 10/1998 |
| WO | WO 98/50053 | 11/1998 |
| WO | WO 98/51788 | 11/1998 |
| WO | WO 99/36545 | 7/1999 |
| WO | WO 99/41359 | 8/1999 |

OTHER PUBLICATIONS

Herman J. C. Berendsen, A Glimpse of the Holy Grail?, Oct. 23, 1998, vol. 282, Science.*
Cuillel et al., *Virology,* 175 (1), 222–231 (Mar. 1990).
Mullis et al., *J. Virol.,* 64 (11). 5317–5323 (Nov. 1990).
Novelli et al., *Virology,* 185 (1), 365–376 (Nov. 1991).
Stewart et al., *EMBO J.,* 12 (7), 2589–2599 (Jul. 1993).
Stewart et al., *Cell,* 67, 145–154 (Oct. 4, 1991).
Taródi, et al., *J. Gen. Virol.,* 62 (2), 379–383 (Oct. 1982).
Tsuzuki et al., *Virology,* 129 (2), 529–533 (Sep. 1983).
Albiges–Rizo et al., *Journal of Biological Chemistry,* 266(6), 3961–3967 (1991).
Bai et al., *Journal of Virology,* 67(9), 5198:5205 (1993).
Bergelson et al., *J. Virol.,* 72 (1), 415–419 (1998).
Bouri et al., *Hum Gene Ther.,* 10 (10), 1633–1640 (1999).
Crawford–Miksza et al., *Virology,* 224, 357–367 (1996).
Crompton et al., *J. Gen. Virol.,* 75, 133–139 (1994).
Einfeld et al., *J Virol.,* 73 (11), 9130–9136 (1999).
Foreman et al., *Hum Gene Ther.,* 9 (9), 1313–1321 (1998).
Gonzalez et al., *Gene Ther.,* 6 (3), 314–320 (1999).

(List continued on next page.)

*Primary Examiner*—David Guzo
*Assistant Examiner*—Gerald G. Leffers, Jr.
(74) *Attorney, Agent, or Firm*—Leydig, Voit & Mayer, Ltd.

(57) ABSTRACT

The present invention provides a recombinant protein having an amino terminus of an adenoviral fiber protein and having a trimerization domain. A fiber incorporating such a protein exhibits reduced affinity for a native substrate than does a wild-type adenoviral fiber trimer. The present invention further provides an adenovirus incorporating the recombinant protein of the present invention.

60 Claims, 2 Drawing Sheets

OTHER PUBLICATIONS

Gonzalez et al., *Hum Gene Ther.,* 10 (16), 2709–2717 (1999).
Hirari et al., *Gene Ther.,* 6 (5), 801–807 (1999).
Hidaka et al., *J Clin Invest.,* 103 (4), 579–587 (1999).
Hong et al., *Virology,* 185(2), 758–767 (1991).
Karayan et al., *Virology,* 202, 782–785 (1994).
Kirby et al., *J. Virol.,* 73 (11), 9508–9514 (1999).
Kleiboecker et al., *Virus Research,* 39, 299–309 (1995).
Kovesdi et al., *Curr Opin Biotechnol.,* 8 (5), 583–589 (Review) (1997).
Mastrangeli et al., *Human Gene Therapy,* 7, 79–87 (1996).
Mathias et al., *Journal of Virology,* 68(10), 6811–6814 (1994).
Michael et al., *Gene Therapy,* 2, 660–668 (1995).
Michael et al., presented at Adenovirus Workshop: St. Andrews University, p. 52 (Jul. 13–15, 1995).
Nemerow et al., *Trends In Cell Biology,* 4, 52–55 (1994).
Roelvink et al., *J Virol.,* 70 (11), 7614–7621 (1996).
Roelvink et al., *Science,* 286 (5444), 1568–1571 (1999).
Roelvink et al., *J. Virol.,* 72 (10), 7909–7915 (1998).
Signäs et al., *Journal of Virology,* 53(2), 672–678 (1985).
Wickham et al., *Cell,* 73 (2), 309–319 (1993).
Wickham et al., *Journal of Cell Biology,* 127(1), 257–264 (1994).
Wickham et al., *Biotechnol Prog.,* 11 (2), 164–170 (1995).
Wickham et al., *Gene Ther.,* 2 (10), 750–756 (1995).
Wickham et al., *Nat Biotechnol.,* 14 (11), 1570–1573 (1996).
Wickham et al., *J. Virol.,* 70 (10), 6831–6838 (1996).
Wickham et al., *Journal of Virology,* 71 (11), 8221–8229 (1997).
Wickham, *Nat Biotechnol.,* 15 (8), 717 (1997).
Wickham et al., *J Virol.,* 71 (10), 7663–7669 (1997).
Wickham et al., *Cancer Immunol Immunother.,* 45 (3–4), 149–151 (1997).
Hong et al., *Tumor Virus Meeting on SV40, Polyoma, and Adenoviruses,* Aug. 15–19, 1990, Cold Spring Harbor, NY, p. 146 (1990).
Javier et al., *Science,* 257, 1267–1271 (Aug. 28, 1992).

* cited by examiner

ALTERNATIVELY TARGETED ADENOVIRUS

CROSS-REFERENCE TO RELATED PATENT APPLICATIONS

This patent application claims the benefit of U.S. Provisional Patent Application Nos. 60/099,851, filed Sep. 11, 1998, and No. 60/136,529, filed May 28, 1999.

TECHNICAL FIELD OF THE INVENTION

The present invention relates to an alternately targeted adenovirus and includes methods for producing and purifying such viruses as well as protein modifications mediating alternate targeting.

BACKGROUND OF THE INVENTION

The various physiological responses of a host animal to the presence of a virus depend on the different ways such viruses interact with the host animal, each of which is first mediated by the surface of the virus ("the virion"). The adenoviral virion is a non-enveloped icosahedron about 65–80 nm in diameter (Horne et al., *J. Mol. Biol.*, 1, 84–86 (1959)). It comprises 252 capsomeres—240 hexons and 12 pentons (Ginsberg et al., *Virology*, 28, 782–83 (1966))—derived from three viral proteins (proteins II, III, and IV) (Maizel et al., *Virology*, 36, 115–25 (1968); Weber et al., *Virology*, 76, 709–24 (1977)). Proteins IX, VI, and IIIa, also present, stabilize the virion (Stewart et al., *Cell*, 67, 145–54 (1991); Stewart et al., *EMBO J.*, 12(7), 2589–99 (1993)).

The hexon provides structure and form to the capsid (Pettersson, in *The Adenoviruses*, pp. 205–270, Ginsberg, ed., (Plenum Press, New York, N.Y., 1984)), and is a homotrimer of the protein II (Roberts et al., *Science*, 232, 1148–1151 (1986)). The hexon provides the main antigenic determinants of the virus, and it also contributes to the serotype specificity of the virus (Watson et al., *J. Gen. Virol.*, 69, 525–35 (1988); Wolfort et al., *J. Virol.*, 62, 2321–28 (1988); Wolfort et al., *J. Virol.*, 56, 896–903 (1985); Crawford-Miksza et al., *J. Virol.*, 70, 1836–44 (1996)).

The hexon trimer is comprised of a pseudohexagonal base and a triangular top formed of three towers (Roberts et al., supra; Athappilly et al., *J. Mol. Biol.*, 242, 430–455 (1994)). The base pedestal consists of two tightly packed eight-stranded antiparallel beta barrels stabilized by an internal loop. The predominant antigenic and serotype-specific regions of the hexon appear to be in loops 1 and 2 (i.e., LI or l1, and LII or l2, respectively), within which are seven discrete hypervariable regions (HVR1 to HVR7) varying in length and sequence between adenoviral serotypes (Crawford-Miksza et al., supra).

The penton contains a base, which is bound to the capsid, and a fiber, which is non-covalently bound to and projects from, the penton base. The penton base, consisting of protein III, is highly conserved among serotypes of adenovirus, and (except for the enteric adenovirus Ad40 and Ad41) it has five RGD tripeptide motifs (Neumann et al., *Gene*, 69, 153–57 (1988)). These RGD tripeptides apparently mediate adenoviral binding to $\alpha_v$ integrins, a family of a heterodimeric cell-surface receptors that also interact with the extracellular matrix and play important roles in cell signaling (Hynes, *Cell*, 69, 11–25 (1992)). These RGD tripeptides also play a role in endocytosis of the virion (Wickham et al. (1993), supra; Bai et al., *J. Virol.*, 67, 5198–3205 (1993)).

The adenoviral fiber is a homotrimer of the adenoviral polypeptide IV (Devaux et al., *J. Molec. Biol.*, 215, 567–88 (1990)), which has three discrete domains. The amino-terminal "tail" domain attaches non-covalently to the penton base. A relatively long "shaft" domain, comprising a variable number of repeating 15 residue β-sheets motifs, extends outwardly from the vertices of the viral particle (Yeh et al., *Virus Res.*, 33, 179–98 (1991)). Lastly, about 200 residues at the carboxy-terminus form the "knob" domain. Functionally, the knob mediates both primary viral binding to cellular proteins and fiber trimerization (Henry et al., *J. Virol.*, 68(8), 5239–46 (1994)). Trimerization also appears necessary for the amino terminus of the fiber to properly associate with the penton base (Novelli et al., *Virology*, 185, 365–76 (1991)). In addition to recognizing cell receptors and binding the penton base, the fiber contributes to serotype integrity and mediates nuclear localization. Moreover, adenoviral fibers from several serotypes are glycosylated (see, e.g., Mullis et al., *J. Virol.*, 64(11), 5317–23 (1990); Hong et al., *J. Virol.*, 70(10), 7071–78 (1996); Chroboczek et al., *Adenovirus Fiber*, p. 163–200 in "The Molecular Repertoire of Adenoviruses I. Virion Structure and Function," W. Doerfler and P. Böhm, eds. (Springer, N.Y. 1995)).

Fiber proteins from different adenoviral serotypes differ considerably. For example, the number of shaft repeats differs between adenoviral serotypes (Green et al., *EMBO J.*, 2, 1357–65 (1983)). Moreover, the knob regions from the closely related Ad2 and Ad5 serotypes are only 63% similar at the amino acid level (Chroboczek et al., *Virology*, 186, 280–85 (1992)), and Ad2 and Ad3 fiber knobs are only 20% identical (Signas et al., *J. Virol.*, 53, 672–78 (1985)). In contrast, the penton base sequences of Ad5 and Ad2 are 99% identical. Despite these differences in the knob region, a sequence comparison of even the Ad2 and Ad3 fiber genes demonstrates distinct regions of conservation, most of which are also conserved among the other human adenoviral fibers (see, e.g., FIGS. 1 and 2).

One interaction between the adenoviral virion and the host animal is the process of cellular infection, during which the wild-type virion first binds the cell surface by means of a cellular adenoviral receptor (AR) (e.g., the coxsackievirus and adenovirus receptor (CAR), the MHC class I receptor, etc. (Bergelson et al., *Science*, 275, 1320–23 (1997); Tanako et al., *Proc. Nat. Acad. Sci. (USA)*, 94, 3352–56 (1997)), Hong et al., *EMBO J.*, 16(9), 2294–06 (1997)). After attachment to an AR, the virus binds $\alpha_v$ integrins. Following attachment to these cell surface proteins, infection proceeds by receptor-mediated internalization of the virus into endocytotic vesicles (Svensson et al., *J. Virol.*, 51, 687–94 (1984); Chardonnet et al., *Virology*, 40, 462–77 (1970)). Within the cell, virions are disassembled (Greber et al., *Cell*, 75, 477–86 (1993)), the endosome disrupted (Fitzgerald et al., *Cell*, 32, 607–17 (1983)), and the viral particles transported to the nucleus via the nuclear pore complex (Dales et al., *Virology*, 56, 465–83 (1973)). As most adenoviral serotypes interact with cells through broadly disseminated cell surface proteins, the natural range of host cells infected by adenovirus is broad.

In addition to cellular infection, host animals react defensively to the presence of adenoviral virions through mechanisms that reduce the effective free titer of the virus. For example, host immune systems, upon exposure to a given adenoviral serotype, can efficiently develop neutralizing antibodies, greatly reducing the effective free titer of the virus upon repeat administration (see, e.g., Setoguchi et al., *Am. J. Respir. Cell. Mol. Biol.*, 10, 369–77 (1994); Kass-Eisler et al., *Gene Ther.*, 1, 395–402 (1994); Kass-Eisler et al., *Gene Ther.*, 3, 154–62 (1996)). Interestingly, such antibodies typically are directed against the same determinants of adenoviral serotype specificity, and are primarily directed to the hypervariable hexon regions and, to some extent, fiber and penton base domains (Watson et al., supra; Wolfort et al. (1988), supra; Wolfort et al. (1985), supra; Crawford-Miksza et al., supra). Of course, the presence of adenoviruses agglutinates red blood cells in humans in a serotype-dependent manner (Hierholzer, *J. Infect. Diseases*, 123(4), 541–50 (1973)). Additionally, adenoviral virions are actively scavenged from the circulation by cells of the reticuloendothelial system (RES) (see, e.g., Worgall et al., *Hum Gene Ther.*, 8, 1675–84 (1997); Wolff et al., *J. Virol.*, 71(1), 624–29 (1997)). In such a response, Kupffer cells, endothelial liver cells, or other RES cells scavenge the virus from the circulation (see generally, Moghini et al., *Crit. Rev. Ther. Drug Carrier Sys.*, 11(1), 31–59 (1994); Van Rooijen et al., *J. Leuk. Biol.*, 62, 702–09 (1997)). For example, virions can become opsonized, possibly though interaction between collectins and glycocylated viral proteins, triggering recognition by such RES cells; alternatively, such cells may recognize charged amino acid residues on the virion surface (see Hansen et al., *Immunobiol.*, 199(2), 165–89 (1998); Jahrling et al., *J. Med. Virol.*, 12(1), 1–16 (1983)).

Based on the popularity of adenoviruses as gene transfer vectors, efforts have been made to increase the ability of adenovirus to enter certain cells, e.g., those few cells it does not infect, an approach referred to as "targeting" (see, e.g., International Patent Application WO 95/26412 (Curiel et al.), International Patent Application WO 94/10323 (Spooner et al.), U.S. Pat. No. 5,543,328 (McClelland et al), International Patent Application WO 94/24299 (Cotten et al.)). Of course, while the ability to target adenoviruses to certain cell types is an important goal, far more desirable is an adenovirus which infects only a desired cell type, an approach referred to as "alternative targeting." However, to exclusively target a virus, its native affinity for host cell ARs must first be abrogated, producing a recombinant adenovirus incapable of productively infecting the full set of natural adenoviral target cells. Efforts aimed at abrogating native adenoviral cell affinity have focused logically on changing the fiber knob. These efforts have been proven disappointing, largely because-they fail to preserve the important fiber protein functions of stable trimerization and penton base binding (Spooner et al., supra). Moreover, replacement of the fiber knob with a cell-surface ligand (McClelland et al., supra) produces a virus only suitable for infecting a cell type having that ligand. Such a strategy produces a virus having many of the same targeting problems associated with wild-type adenoviruses (in which fiber trimerization and cellular tropism are mediated by the same protein domain), thus decreasing the flexibility of the vector. Moreover, due to the necessity of having a propagating cell line, and the integral connection between the fiber trimerization and targeting functions, obtaining a mutant virus with substituted targeting is difficult. For example, removing the fiber knob and replacing it with a non-trimerizing ligand (e.g., Spooner et al., McClelland et al., supra) results in a virus lacking appreciable fiber protein.

Aside from the broad natural tropism of the virus noted above, the non-infectious interactions between adenovirus and the host also pose problems for using adenovirus as gene transfer vectors. Such interactions effectively reduce the free titer of a given dose of adenovirus beneath that which is clinically effective. As such, there is currently a need for an adenovirus exhibiting reduced affinity for such natural interactions with a host animal (e.g., target cell affinity, innate or acquired immune survailence, etc). Moreover, there is a need for such a virus which is able to deliver and express a desired transgene within a predefined tissue—an alternatively targeted virus.

BRIEF SUMMARY OF THE INVENTION

The present invention provides a recombinant protein having an amino terminus of an adenoviral fiber protein and having a trimerization domain. A fiber incorporating such a protein exhibits reduced affinity for a native substrate than does a wild-type adenoviral fiber trimer. The present invention further provides an adenovirus incorporating the recombinant protein of the present invention.

The present invention is useful in a variety of gene-transfer applications, in vitro and in vivo, as a vector for delivering a desired gene to a cell with minimal ectopic infection. Specifically, the present invention permits more efficient production and construction of safer vectors for gene transfer applications. The present invention is also useful as a research tool by providing methods and reagents for the study of adenoviral attachment and infection of cells and in a method of assaying receptor-ligand interaction. Similarly, the recombinant fiber protein can be used in receptor-ligand assays and as adhesion proteins in vitro or in vivo. Additionally, the present invention provides reagents and methods permitting biologists to investigate the cell biology of viral growth and infection. Thus, the vectors of the present invention are highly useful in biological research.

DETAILED DESCRIPTION OF THE INVENTION

Recombinant Protein

Figure 1:
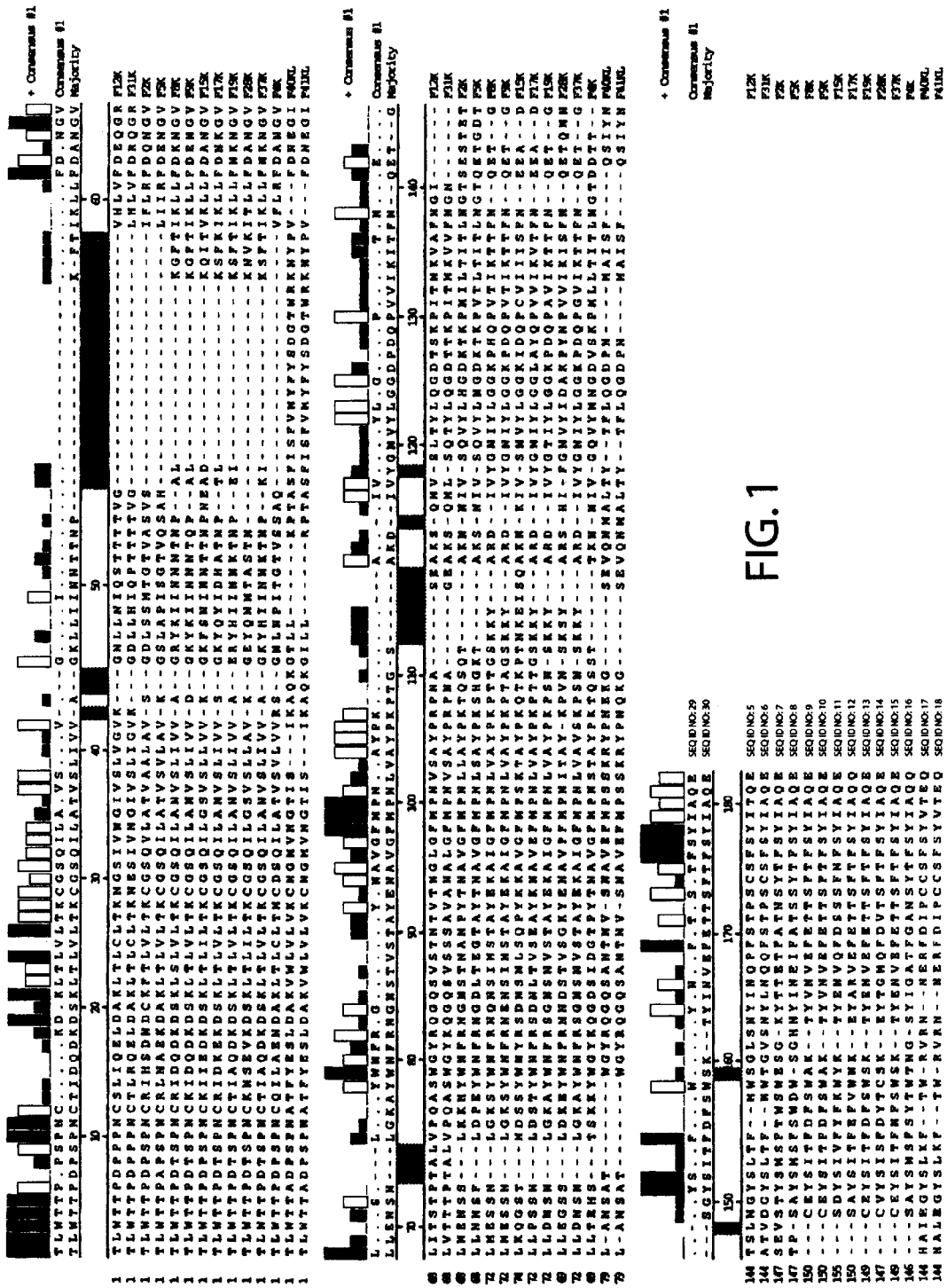
FIG. 1 (Panels A–B) sets forth a comparison of the amino acid sequences of the non-group B serotype fiber knobs (SEQ ID NOs: 5–18) using the Clustal method with PAM100 residue weight table. The height of the bars at the top of each row of sequence comparison correlates to the degree of homology. Consensus and majority sequences are indicated as SEQ ID NOs: 29 and 30, respectively.

The present invention provides a recombinant adenoviral fiber protein having an amino terminus derived from an adenoviral fiber protein and having a trimerization domain. A trimer including such a recombinant protein exhibits reduced affinity for a native substrate, such as an antibody, collecting, opsins, a cellular binding site, etc. (i.e., native to the serotype from which the shaft, and particularly the amino-terminus, is drawn) as compared to a native adenoviral fiber trimer. The trimer can be a homotrimer or a heterotrimer of different fiber monomers. Any modification of the monomeric units reducing the affinity of the resulting trimer for its native cell surface binding site (i.e., a native AR) is within the scope of the invention. Preferably, the reduction in affinity is a substantial reduction in affinity (such as at least an order of magnitude, and preferably more) relative to the unmodified corresponding fiber.

As mentioned, where a trimerization domain is itself a ligand for a native cell surface binding site, fiber proteins possessing such trimerization domains present some of the same problems for targeting as native adenoviral fiber trimerization domains. Therefore, the trimerization domain of the inventive protein invention preferably is not a ligand for the CAR or MHC-1 cell surface proteins. Most preferably, the non-native trimerization domain is not a ligand for any native adenoviral cell-surface binding site, whether the site is an AR or other cell surface binding site. As is discussed herein, adenoviruses incorporating such proteins exhibit reduced ability to appreciably infect cells via native AR proteins, and can serve as efficient source vectors for engineering alternatively targeted vectors. Therefore, while the trimerization domain preferably is not a ligand for a cell surface binding site, the entire trimer can be such a ligand (e.g., by virtue of a non-native ligand as discussed herein). Moreover, the trimerization domain can be a ligand for a substrate other than a native cell surface binding site, as such trimerization-ligands do not present the same concern for cell targeting as do trimerization domains which are ligands for cell surface binding sites. Thus, for example, the non-native trimerization domain can be a ligand for a substrate on an affinity column, on a blood-borne molecule, or even on a cell surface when it is not a native cell-surface binding site (e.g., on a cell engineered to express a substrate cell surface protein not native to the unmodified cell type).

The recombinant fiber protein can lack a sizable number of residues, or even identifiable domains, as herein described. For example, the protein can lack the native knob domain; it can lack one or more native shaft β-sheet repeats, or it can be otherwise truncated. Thus, a recombinant fiber protein can have any desired modification so long as it trimerizes when produced by a eukaryotic cell. Furthermore, a recombinant fiber protein preferably is not modified appreciably at the amino terminus (e.g., the amino-terminus of a monomer preferably consists essentially of the native fiber amino-terminus) to ensure that a fiber incorporating the recombinant fiber protein interacts properly with the penton base. Hence, the present invention also provides a composition of matter comprising a recombinant fiber protein of the present invention and an adenoviral penton base. Preferably, the recombinant fiber protein and the penton base associate much in the same manner as wild-type fibers and penton bases. Of course, the penton base can also be modified, for example, to include a non-native ligand, for example as is described in U.S. Pat. No. 5,559,099 (Wickham et al.).

In one embodiment, the fiber is modified to render it less able to interact with the innate or acquired host immune system. For example, one or more amino acids of the native fiber protein can be mutated to render the recombinant fiber protein less able to be recognized by neutralizing antibodies than a wild-type fiber (see, e.g., International Patent Application WO 98/40509 (Crystal et al.). The fiber also can be modified to lack one or more amino acids mediating interaction with the RES. For example, the fiber can be mutated to lack one or more glycosylation or phosphorylation sites, or the fiber (or virus containing the fiber) can be produced in the presence of inhibitors of glycosylation or phosphorylation. Similarly, the fiber (or other protein within the virus) can be conjugated to a lipid derivative of polyethylene glycol (PEG) comprising a primary amine group, an epoxy group, or a diacylclycerol group (see, e.g., Kilbanov et al., *FEBS Lett.*, 268, 235 (1990); Senior et al., *Biochem. Biophys. Acta.*, 1062, 11 (1991); Allen et al., *Biochem. Biophys. Acta.*, 1066, 29 (1991); Mori et al., *FEBS Lett.*, 284, 263 (1991)) to avoid collectin and/or opsonin binding or scavenging by Kupffer (or other RES) cells.

A recombinant fiber protein lacking one or more amino acids, as herein described, can optionally comprise a non-native residue (e.g., several non-native amino acids) in addition to (i.e., insertions) or in place of (i.e., substitutions) the missing native amino acid(s); of course, alternatively, the native amino acid(s) can be deleted from the knob. Preferably, the amino-acid is substituted with another non-native amino acid to preserve topology and, especially, trimerization. Moreover, if substituted, the replacement amino acid preferably confers novel qualities to the recombinant fiber protein. For example, to maximally ablate binding to the native substrate, a native amino acid can be substituted with a residue (or a plurality of residues) having a different charge. Such a substitution maximally interferes with the electrostatic interaction between native adenoviral knob domains and cellular ARs or interferes with a conformational change required to efficiently bind an AR or elements of the RES. Similarly, a native amino acid can be substituted with a residue (or a plurality of residues) of differing weight, where possible. For example, substitution with a heavier residue maximally interferes with the steric interaction between adenoviral domains and native substrates, by virtue of the longer side-chains on such heavier residues.

Any native amino-acid residue mediating or assisting in the interaction between the knob and a native cellular AR is a suitable amino acid for mutation or deletion from the recombinant fiber protein. Such amino acid need not itself be the site of contact between the fiber and the receptor. For example, the native amino acid might be involved in a conformational change associated with receptor binding. The inventive fiber protein can lack any number of such native amino acids, so long as, in the aggregate, the recombinant fiber protein can associate to form a trimer. The amino acid can be within a β-sheet of the knob or within a loop connecting two -sheets (such as, for example, the AB, BC, CD, DE, EF, FG, GH, HI, or IJ loops). Indeed, the amino acid can be within 10 (e.g., within 5) residues of a β sheet or a loop. In the mature, folded trimer of the present invention, the amino acid can be within about 10 nm (e.g., within about 5 nm or even within about 2 nm) of a β sheet or a loop.

Native amino acid residues for modification or deletion can be selected by any method. For example, the sequences from different adenoviral serotypes (which are known in the art) can be compared to deduce conserved residues likely to mediate AR-binding. Alternatively or in combination, the sequence can be mapped onto a three dimensional representation of the protein (such as the crystal structure) to deduce those residues most likely responsible for AR binding. These analyses can be aided by resorting to any common algorithm or program for deducing protein structural functional interaction. Alternatively, random mutations can be introduced into a cloned adenoviral fiber expression cassette. One method of introducing random mutations into a protein is via the Taq polymerase. For example, a clone encoding the fiber knob (see, e.g., Roelvink et al., *J. Virol.*, 70, 7614–21 (1996)) can serve as a template for PCR amplification of the adenoviral fiber knob, or a portion thereof. By varying the concentration of divalent cations in the PCR reaction, the error rate of the transcripts can be largely predetermined (see, e.g., Weiss et al., *J. Virol.*, 71, 4385–94 (1997); Zhou et al., *Nucl. Acid. Res.*, 19, 6052 (1991)). The PCR products then can be subcloned back into the template vector to replace the sequence within the fiber coding sequence employed as a source for the PCR reaction, thus generating a library of fibers, some of which will harbor mutations which diminish native AR binding while retaining the ability to trimerize.

Figure 2:
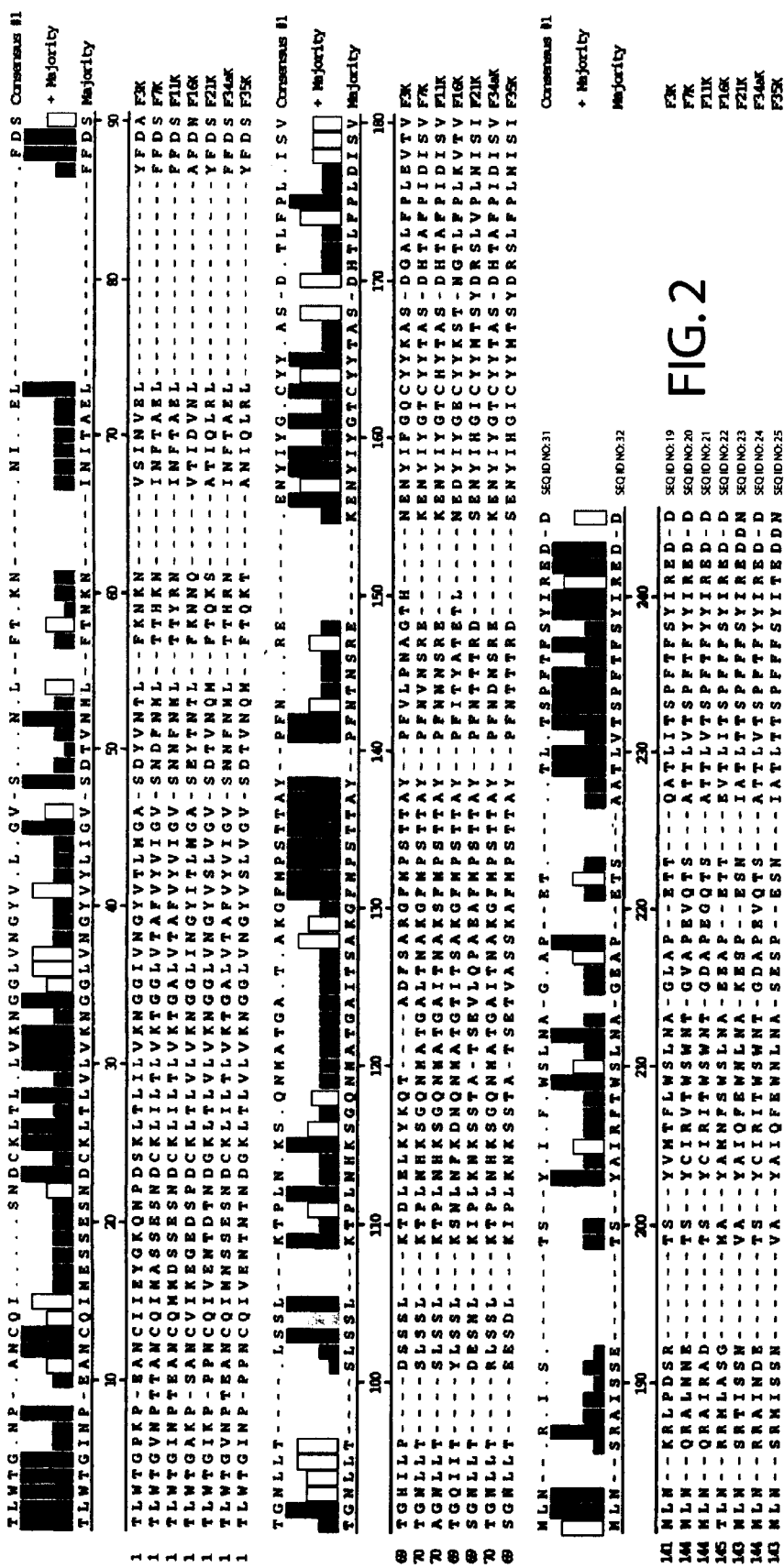
FIG. 2 (Panels A–B) sets forth a comparison of the amino acid sequences of the group B serotype fiber knobs (SEQ ID NOs: 19–25) using the J. Hein method with PAM250 residue weight The height of the bars at the top of each row of sequence comparison correlates to the degree of homology. Consensus and majority sequences are indicated as SEQ ID NOs: 31 and 32, respectively.

The amino acids of knobs from strains other than Ad5 that correspond to these listed residues are apparent upon a comparison between the sequences of the fibers of different adenoviral strains, and any suitable method of determining such correspondence can be employed (e.g., Clusal method with PAM100 residue weight table, J. Hain method with PAM250 residue weight table, etc.). Examples of such sequence comparison of the knobs of Ad fiber proteins (SEQ ID NOs:5–25) are set forth in FIGS. 1 and 2. By such comparison, residues (e.g., conserved) from other scrotypes which, mutated as described, result in fiber trimers with reduced AR binding can be identified (see, e.g., SEQ ID NOs: 29–32). Thus, for example, for CAR-binding fibers, preferably, the amino acid(s) to be mutated is within 10 (e.g., within about 5) amino acids or within about 10 nm (e.g., within about 5 nm) of an amino acid corresponding to residues 404–406, 408, 409, 412–417, 420, 439, 441, 442, 449–454, 456, 458, 460, 462, 466, 467, 469–472, 474–477, 482, 485, 487–492, 505–512, 515, 517, 519, 521–528, 533, 535, 537–549, 551, 553, 555, 559–568, 580, or 581 of the native Ad5 fiber protein (SEQ ID NO:1). More preferably, the amino acid(s) to be mutated correspond to at least one of these residues, such as amino acid 189, 190, 198, 201, or 262 of the native Ad9 fiber protein (SEQ ID NO:3) or amino acid 395, 396, 404, 407, or 470 of the native Ad41 long fiber protein (SEQ ID NO:2). Even more preferably, the mutant fiber protein comprises at least one replacement mutation of a residue corresponding to residues 408, 409, 412–417, 420, 477, or 487–491 of the native Ad5 fiber protein or at least one deletion mutation of a residue corresponding to residues 474–477 or 489–492 of the native Ad5 fiber protein. Similarly, for group B fibers, the amino acid(s) to be mutated is within 10 (e.g., within about 5) amino acids or within about 10 nm (e.g., within about 5 nm) of an amino acid corresponding to residues 136, 155, 177, 181, 198, 210, 211, 215, 233, 234, 236, 238, 248, 257, 260, 261, 276, 284, 302, 303, 317, or 318 of the native Ad3 fiber protein (SEQ ID NO:4).

The recombinant fiber protein of the present invention can be produced by any suitable method. For example, the mutant fiber protein can be synthesized using standard direct peptide synthesizing techniques (e.g., as summarized in Bodanszky, *Principles of Peptide Synthesis* (Springer-Verlag, Heidelberg: 1984)), such as via solid-phase synthesis (see, e.g., Merrifield, *J. Am. Chem. Soc.*, 85, 2149–54 (1963); and Barany et al., *Int. J. Peptide Protein Res.*, 30, 705–739 (1987)). Alternatively, site-specific mutations can be introduced into the recombinant fiber protein by ligating into an expression vector a synthesized oligonucleotide comprising the modified site. Alternatively, a plasmid, oligonucleotide, or other vector encoding the desired mutation can be recombined with the adenoviral genome or with an expression vector encoding the recombinant fiber protein to introduce the desired mutation. Oligonucleotide-directed site-specific mutagenesis procedures also are appropriate (e.g., Walder et al., *Gene*, 42, 133 (1986); Bauer et al., *Gene*, 37, 73 (1985); Craik, *Biotechniques*, 12–19 (1995); U.S. Pat. Nos. 4,518,584 (Mark et al.) and 4,737,462 (Mark et al.)). However engineered, the DNA fragment encoding the recombinant fiber protein can be subcloned into an appropriate vector using well known molecular genetic techniques. The fragment is then transcribed and the peptide subsequently translated in vitro within a host cell. Any appropriate expression vector (e.g., Pouwels et al., *Cloning sectors: A Laboratory Manual* (Elsevier, N.Y.: 1985)) and corresponding suitable host cells can be employed for production of recombinant peptides. Expression hosts include, but are not limited to, bacterial species, yeast, mammalian or insect host cell systems including baculovirus systems (e.g., Luckow et al., *Bio/Technology*, 6, 47 (1988)), and established cell lines such HEK-293, COS-7, C127, 3T3, CHO, HeLa, BHK, etc. An especially preferred expression system for preparing modified fibers of the invention is a baculovirus expression system (Wickham et al., *J. Virol.*, 70, 6831–38 (1995)) as it allows the production of high levels of recombinant proteins. Of course, the choice of expression host has ramifications for the type of peptide produced, primarily due to post-translational modification.

Once produced, the recombinant fiber proteins are assayed for fiber protein activity. Specifically, the ability of recombinant fiber protein to form trimers, interact with the penton base, and interact with native substrate's (e.g., antibodies, ARs, opsonins, collecting, RES cells, etc.) is assayed. Any suitable assay can be employed to measure these parameters. For example, as improperly folded monomers are generally insoluble (Scopes, "Protein Purification" (3d Ed., 1994), Chapter 9, p. 270–82 (Springer-Verlag, New York)), one assay for trimerization is whether the recombinant fiber is soluble. Determining solubility of the fiber is aided if an amount of radioactive amino-acid is incorporated into the protein during synthesis. Lysate from the host cell expressing the recombinant fiber protein can be centrifuged, and the supernatant and pellet can be assayed via a scintillation counter or by Western analysis. Subsequently, the proteins within the pellet and the supernatant are separated (e.g., on an SDS-PAGE gel) to isolate the fiber protein for further assay. Comparison of the amount of fiber protein isolated from the pellet vis-a-vis the fiber protein isolated from the supernatant indicates whether the mutant protein is soluble. Alternatively, trimerization can be assayed by using a monoclonal antibody recognizing only the amino portion of the trimeric form of the fiber (e.g., via immunoprecipitation, Western blotting, etc.). Another measure of trimerization is the ability of the recombinant fiber to form a complex with the penton base (Novelli and Boulanger, *Virology*, 185, 1189 (1995)), as only fiber trimers can so interact. This propensity can be assayed by co-immunoprecipitation, gel mobility-shift assays, SDS-PAGE (boiled samples migrate as monomers, otherwise, they migrate as larger proteins), etc. Yet another measure of trimerization is to detect the difference in molecular weight of a trimer as opposed to a monomer. For example, a boiled and denatured trimer will run as a lower molecular weight than a non-denatured stable trimer (Hong and Angler, *J. Virol.*, 70, 7071–78 (1996)). A trimeric recombinant fiber also can be assayed for its ability to bind native substrates. For example, modification of fiber to interfere with its interaction with the host innate or acquired immune system can be accomplished by measuring the free titer of the virus over time. This can be assessed by measuring serum half life, tropism to organs associated with the RES (e.g., liver in mice and humans, lung in pigs, etc.), by agglutination of red blood cells, or by detection of adenoviral genetic material in cell samples.

A trimeric recombinant fiber also can be assayed for its ability to bind native ARs. Any suitable assay that can detect this characteristic is sufficient for use in the present invention. A preferred assay involves exposing cells expressing a native AR (e.g., HEK-293 cells) to the recombinant fiber trimers under standard conditions of infection. Subsequently, the cells are exposed to native adenoviruses, and the ability of the viruses to bind the cells is monitored. Monitoring can be by autoradiography (e.g., employing radioactive viruses), immunocytochemistry, or by measuring the level of infection or gene delivery (e.g., using a reporter gene). In contrast with native trimers which reduce or substantially eliminate subsequent viral binding to the HEK-293 cells, those trimers not substantially reducing the ability of native adenoviruses to subsequently bind the cells are trimers of the present invention. The reduction of interference with subsequent viral binding indicates that the trimer is itself not a ligand for its native mammalian AR, or at least binds with reduced affinity.

Alternatively, a vector including a sequence encoding a mutated fiber (or a library of putative mutated fibers, such as described herein) can be introduced into a suitable host cell strain to express the fiber protein, and, mutants can be identified by assaying the inability to bind the soluble CAR protein (e.g., by probing a replica lift with radiolabeled CAR or by other suitable method). Because a reduction in CAR-binding could be due to either selective ablation of the ligand or structural modification affecting trimerization. mutant fibers identified as non-CAR binding by such a library screen must be assayed for the ability to trimerize, as described above.

Virion and Virus

The present invention provides an adenoviral virion incorporating the recombinant fiber protein of the present invention. The virion does not interact with native substrates (e.g., innate and acquired immune systems, cell-surface proteins, etc.) as readily as the wild-type serotype, due to the above-mentioned reduction in affinity of the fibers present in the virion. Moreover, the virion can be further modified to reduce interaction with native substrates through the inclusion of other recombinant proteins. Thus, for example, the virion can include one or more recombinant penton base proteins lacking a native RGD sequence to reduce cell binding via $\alpha_v$ integrins (see, e.g., U.S. Pat. Nos. 5,559,099 (Wickham et al.) and 5,731,190 (Wickham et al.)). Similarly, the virion can include one or more recombinant hexons lacking a native sequence (e.g., HVR) to reduce its ability to be recognized by a neutralizing antibody (see, e.g., International Patent Application WO 98/40509 (Crystal et al.)). Also, the virion can be modified to reduce its ability to interact with the RES. For example, the virion proteins can be mutated to lack one or more glycosylation or phosphorylation sites, or it can be produced in the presence of inhibitors of glycosylation or phosphorylation. Similarly, the virion proteins can be conjugated to a lipid derivative of PEG comprising a primary amine group, an epoxy group, or a diacylclycerol group, as discussed above, to reduce collectin and/or opsonin affinity or scavenging by Kupffer cells or other cells of the RES. Such modifications reduce the ability of host animals to develop neutralizing antibodies to the virions, thereby permitting repeat administration of the virions.

While the virion exhibits reduced affinity for natural adenoviral substrates, it can include one or more non-adenoviral ligands, for example, to effect targeted infection of a population of cells other than that for which adenoviruses are naturally tropic. Additionally, the non-native ligand can be used to purify the virus, to inactivate the virus (e.g., by adsorbing it to a substrate for the ligand), or to grow the virus on cell lines having receptors recognizing the non-native ligand, for example, as described in International Patent Application WO 98/54346 (Wickham et al.).

The virus can include any suitable ligand (e.g., a peptide specifically binding to a substrate). For example, for targeting the adenovirus to a cell type other than that naturally infected (or a group of cell types other than the natural range or set of host cells), the ligand can bind a cell surface binding site (e.g., any site present on the surface of a cell with which the adenovirus can interact to bind the cell and thereby promote cell entry). A cell surface binding site can be any suitable type of molecule, but typically is a protein (including a modified protein such as a glycoprotein, a mucoprotein, etc.), a carbohydrate, a proteoglycan, a lipid, a mucin molecule, or other similar molecule. Examples of potential cell surface binding sites include, but are not limited to, heparin and chondroitin sulfate moieties found on glycosaminoglycans; sialic acid moieties found on mucins, glycoproteins, and gangliosides; common carbohydrate molecules found in membrane glycoproteins, including mannose, N-acetyl-galactosamine, N-acetyl-glucosamine, fucose, and galactose; glycoproteins such cell adhesion molecules (CAMs) (e.g., ICAM-1, ICAM-2, ICAM-3, VCAM-1, NCAM), selectins (e.g., E-selectin, P-selectin, L-selectin, etc.), CD, cadherins, TNF family receptors, GPI-linked receptors, receptors that are efficiently internalized (e.g., CD44, CD31 on endothelial cells, CD34 on high endo-venules), endoglin, growth factor receptors, PSA, androgen receptors, glucocorticoid receptors, prostate-specific membrane antigen (PSMA), MUC1, MUC234, MUC5AC, MUC5B, MUC7, KSA carcino-embryonic antigen (CEA), HER2/NEU (erbB2), folate receptor, corionic gonadotropin-β, (Zhang et al., *Clin. Cancer Res.*, 4, 2669–76 (1998); *Cancer Res.*, 58, 4055 (1998)), and others are known in the art.

A particular cell surface binding site can be present on a narrow class of cell types (e.g., cardiac muscle, skeletal muscle, smooth muscle, etc.) or a broader group encompassing several cell types. Through integration of an appropriate cell-specific ligand, the virion can be employed to target any desired cell type, such as, for example, neuronal, glial, endothelial (e.g., via tissue factor receptor, FLT-1, CD31; CD36; CD34, CD105, CD13, ICAM-1 (McCormick et al., *J. Biol. Chem.*, 273, 26323–29 (1998)); thrombomodulin receptor (Lupus et al., *Suppl.*, 2, S 120 (1998)); VEGFR-3 (Lymboussaki et al., *Am. J. Pathol.*, 153(2), 395–403 (1998); mannose receptor; VCAM-1 (Schwarzacher et al., *Atherocsclerosis*, 122, 59–67 (1996)), or other receptors); blood clots (e.g., through fibrinogen or aIIbb3 peptide), epithelial (e.g., inflamed tissue through selecting, VCAM-1, ICAM-1, etc.), keratinocytes, follicular cells, adipocytes, fibroblasts, hematopoietic or other stem cells, myoblasts, myofibers, cardiomyocytes, smooth muscle, somatic, osteoclasts, osteoblasts, tooth blasts, chondrocytes, melanocytes, hematopoietic cells, etc., as well as cancer cells derived from any of the above cell types (e.g., prostate (such as via PSMA receptor (see, e.g., Schuur et al., *J. Biol. Chem.*, 271 (12), 7043–7051 (1996); *Cancer Res.*, 58, 4055 (1998))), breast, lung, brain (e.g., glioblastoma), leukemia/lymphoma, liver, sarcoma, bone, colon, testicular, ovarian, bladder, throat, stomach, pancreas, rectum, skin (e.g., melanoma), kidney, etc.). Thus, the inventive virions can be targeted to cells within any organ or system, including, for example, respiratory system (e.g., trachea, upper airways, lower airways, alveoli), nervous system and sensory organs (e.g., skin, ear, nasal, tongue, eye), digestive system (e.g., oral epithelium and sensory organs, salivary glands, stomach, small intestines/duodenum, colon, gall bladder, pancreas, rectum), muscular system (e.g., skeletal muscle, connective tissue, tendons), skeletal system (e.g., joints (synovial cells), osteoclasts, osteoblasts, etc.), immune system (e.g., bone marrow, stem cells, spleen, thymus, lymphatic system, etc.), circulatory system (e.g., muscles connective tissue, and/or endothelia of the arteries, veins, capillaries, etc.), reproductive system (e.g., testis, prostrate, uterus, ovaries), urinary system (e.g., bladder, kidney, urethra), endocrine or exocrine glands (e.g., breasts, adrenal glands, pituitary glands), etc.

In other embodiments (e.g., to facilitate purification or propagation within a specific engineered cell type), the non-native ligand can bind a compound other than a cell-surface protein. Thus, the ligand can bind blood- and/or lymph-borne proteins (e.g., albumin), synthetic peptide sequences such as polyamino acids (e.g., polylysine, polyhistidine, etc.), artificial peptide sequences (e.g., FLAG), and RGD peptide fragments (Pasqualini et al., *J. Cell. Biol.*, 130, 1189 (1995)). The ligand can even bind non-peptide substrates, such as plastic (e.g., Adey et al., *Gene*, 156, 27 (1995)), biotin (Saggio et al., *Biochem. J.*, 293, 613 (1993)), a DNA sequence (Cheng et al., *Gene*, 171, 1 (1996); Krook et al., *Biochem. Biophys., Res. Commun.*, 204, 849 (1994)), streptavidin (Geibel et al., *Biochemistry*, 34, 15430 (1995); Katz, *Biochemistry*, 34, 15421 (1995)), nitrostreptavidin (Balass et al., *Anal. Biochem.*, 243, 264 (1996)), heparin (Wickham et al., *Nature Biotechnol.*, 14, 1570–73 (1996)), cationic supports, metals such as nickel and zinc (e.g., Rebar et al., *Science*, 263, 671 (1994); Qui et al., *Biochemistry*, 33, 8319 (1994)), or other potential substrates.

Examples of suitable ligands and their substrates for use in the method of the invention include, but are not limited to, CR2 receptor binding the amino acid residue attachment sequences, CD4 receptor recognizing the V3 loop of HIV gp120, transferrin receptor and its ligand (transferrin), low density lipoprotein receptor and its ligand, the ICAM-1 receptor on epithelial and endothelial cells in lung and its ligand, linear or cyclic peptide ligands for streptavidin or nitrostreptavidin (Katz, *Biochemistry*, 34, 15421 (1995)), galactin sequences that bind lactose, galactose and other galactose-containing compounds, and asialoglycoproteins that recognize deglycosylated protein ligands. Moreover, additional ligands and their binding sites preferably include (but are not limited to) short (e.g., 6 amino acids or less) linear stretches of amino acids recognized by integrins, as well as polyamino acid sequences such as polylysine, polyarginine, etc. Inserting multiple lysines and/or arginines provides for recognition of heparin and DNA. Also, a ligand can comprise a commonly employed peptide tag (e.g., short amino acid sequences known to be recognized by available antisera) such as sequences from glutathione-S-transferase (GST) from *Shistosoma manosi*, thioredoxin β-galactosidase, or maltose binding protein (MPB) from *E. coli.*, human alkaline phosphatase, the FLAG octapeptide, hemagluttinin (HA) (Wickham et al. (1996), supra), polyoma virus peptides, the SV40 large T antigen peptide, BPV peptides, the hepatitis C virus core and envelope E2 peptides and single chain antibodies recognizing them (Chan, *J. Gen. Virol.*, 77, 2531 (1996)), the c-myc peptide, adenoviral penton base epitopes (Stuart et al., *EMBO J.*, 16, 1189–98 (1997)), epitopes present in the E2 envelope of the hepatitis C virus (see, e.g., Chan et al. (1996), supra), and other commonly employed tags. A preferred substrate for a tag ligand is an antibody directed against it or a derivative of such an antibody (e.g., a FAB fragment, single chain antibody (ScAb)).

As mentioned, a suitable ligand can be specific for any desired substrate, such as those recited herein or otherwise known in the art. However, adenoviral vectors also can be engineered to include novel ligands (e.g., in protein II, III, IIIa, IV, IV, VI, and/or IX) by first assaying for the ability of a peptide to interact with a given substrate. Generally, a random or semirandom peptide library containing potential ligands can be produced, which is essentially a library within an expression vector system. Such a library can be screened by exposing the expressed proteins (i.e., the putative ligands) to a desired substrate. Positive selective binding of a species within the library to the substrate indicates a ligand for that substrate, at least under the conditions of the assay. For screening such a peptide library, any assay able to detect interactions between proteins and substrates is appropriate, and many are known in the art. However, one preferred assay for screening a protein library is a display system (e.g., using an adenovirus or a bacteriophage), which employs a virus expressing the library (e.g., Koivunen et al., *Bio/Technology*, 13, 265–70 (1995); Yanofsky et al., *Proc. Nat. Acad. Sci. U.S.A.*, 93, 7381–86 (1996); Barry et al., *Nature Med.*, 2(3), 299–305 (1996)). Binding of the virus to the substrate is assayed by exposing the virus to the substrate, rinsing the substrate, and selecting for virus remaining bound to the substrate. Subsequently, limiting dilution can identify individual clones expressing the putative ligand. Thereafter, the insert present in such clones can be sequenced to determine the identity of the ligand.

Once a given ligand is identified, it can be incorporated into any location of the virus capable of interacting with a substrate (i.e., the viral surface). For example, the ligand can be incorporated into the fiber, the penton base, the hexon, protein IX, VI, or IIIa, or other suitable location. Where the ligand is attached to the fiber protein, preferably it does not disturb the interaction between viral proteins or monomers. Thus, the ligand preferably is not itself an oligomerization domain, as such can adversely interact with the trimerization domain as discussed above. Preferably the ligand is added to the virion protein, and is incorporated in such a manner as to be readily exposed to the substrate (e.g., at the terminus of the protein, attached to a residue facing the substrate, positioned on a peptide spacer to contact the substrate, etc.) to maximally present the ligand to the substrate. Where the ligand is attached to or replaces a portion of the penton base, preferably it is within the hypervariable regions to ensure that it contacts the substrate. Furthermore, where the ligand is attached to the penton base, preferably. the recombinant fiber is truncated or short (e.g., from 0 to about 10 shaft repeats) to maximally present the ligand to the substrate (see, e.g., U.S. Pat. No. 5,559,099 (Wickham et al.)). Where the ligand is attached to the hexon, preferably it is within a hypervariable region (Miksza et al., *J. Virol.*, 70(3), 1836–44 (1996)).

When engineered into an adenoviral protein, the ligand can comprise a portion of the native sequence in part and a portion of the non-native sequence in part. Similarly, the sequences (either native and/or nonnative) that comprise the ligand in the protein need not necessarily be contiguous in the chain of amino acids that comprise the protein. In other words, the ligand can be generated by the particular conformation of the protein, e.g., through folding of the protein in such a way as to bring contiguous and/or noncontiguous sequences into mutual proximity. Of course an adenovirus of the present invention (or a blocking protein) can comprise multiple ligands, each binding to a different substrate. For example, a virus can comprise a first ligand permitting affinity purification as described herein, a second ligand that selectively binds a cell-surface site as described herein, and/or a third ligand for inactivating the virus, also as described herein.

The protein including the ligand can include other non-native elements as well. For example, a non-native, unique protease site also can be inserted into the amino acid sequence. The protease site preferably does not affect fiber trimerization or substrate specificity of the fiber ligand. Many such protease sites are known in the art. For example, thrombin recognizes and cleaves at a known amino acid sequence (Stenflo et al., *J. Biol. Chem.*, 257, 12280–90 (1982)). The presence of such a protease recognition sequence facilitates purification of the virus in some protocols. The protein can be engineered to include the ligand by any suitable method, such as those methods described above for introducing mutations into proteins.

The virion can be used by itself, for example in studies of viral tropism or binding kinetics. In other embodiments, the virion can be used as a genetic vector. For example, the virion can be used in conjunction with lipids and/or liposomes to deliver exogenous genetic material to target cells, in accordance with well-documented methods. In other embodiments, the virion contains a genome derived from an adenovirus; thus, the invention provides an adenoviral vector including the inventive virion and an adenoviral genome.

The adenoviral vector of the present invention can include one or more non-native amino acid sequences for expression (e.g., "expression cassettes" or "genes") as well. Preferably, the non-native amino acid is capable of being transcribed in a cell into which the vector has been internalized. The non-native amino acid can encode a product that effects a biological (e.g., therapeutic) response either at the cellular level or systemically); alternatively, the non-native nucleic acid sequence can encode a product that, in some fashion, can be detected in a cell (e.g., a "reporter gene"). The non-native amino acid can exert its effect at the level of RNA or protein. For instance, a protein encoded by the non-native amino acid can be employed in the treatment of an inherited disease, such as, e.g., the cystic fibrosis transmembrane conductance regulator cDNA for the treatment of cystic fibrosis. Alternatively, the protein encoded by the non-native amino acid can exert its therapeutic effect by effecting cell death. For instance, expression of the non-native amino acid in itself can lead to cell killing, as with expression of the diphtheria toxin. Alternatively, the expression of the non-native amino acid, can render cells selectively sensitive to the action of certain drugs, e.g., expression of the HSV thymidine kinase gene renders cells sensitive to antiviral compounds including acyclovir, gancyclovir, and FIAU (1-(2-deoxy-2-fluoro-β-D-arabinofuranosil)-5-iodouracil). Moreover, the non-native amino acid can exert its effect at the level of RNA, for instance, by encoding an antisense message or ribozyme, a protein which affects splicing or 3' processing (e.g., polyadenylation), or a protein affecting the level of expression of another gene within the cell (i.e., where gene expression is broadly considered to include all steps from initiation of transcription through production of a processed protein), perhaps, among other things, by mediating an altered rate of mRNA accumulation, an alteration of mRNA transport, and/or a change in post-transcriptional regulation. Of course, where it is desired to employ gene transfer technology to deliver a given non-native amino acid, its sequence will be known in the art.

Where the inventive adenoviral vector includes a non-native amino acid and a non-adenoviral ligand in its virion, the non-native amino acid can be operably linked to any suitable promoter, such as a promoter native to the adenoviral genome or a non-adenoviral promoter. Where the ligand is employed to deliver the vector to a desired cell type, preferably the non-adenoviral promoter is active within the cell type, and more preferably, the non-adenoviral promoter is a tissue-specific promoter (e.g., specific for the cell type to which the ligand binds), such as those cell types discussed above. For example, expression in targeted endothelial cells can be mediated using the E-selectin promoter see, e.g., Whelan et al., *TIBS*, 21, 65–69 (1996)); passenger gene expression in targeted prostate cancer cells can be mediated using the PSA promoter (see, e.g., Schuur et al., *J. Biol. Chem.*, 271(12), 7043–7051 (1996), Pang et al., *Cancer Res.*, 57, 495 (1997)) or the E2F promoter. Furthermore, the promoter can be that for a tissue-specific receptor, such as those receptors mentioned herein, still other tissue specific promoter systems are known in the art. Alternatively, the non-native amino acid can be placed under control of a regulable promoter (e.g., metallothionein promoter, tetracycline-responsive promoter, RU486-responsive promoter, etc.).

The altered protein (e.g., the recombinant fiber protein or the coat protein having the ligand) and the non-native amino acid where present) can be incorporated into the adenovirus by any suitable method, many of which are known in the art. As mentioned herein, the protein is preferably identified by assaying products produced in high volume from genes within expression vectors (e.g., baculovirus vectors). The genes from the vectors harboring the desired mutation can be readily subcloned into plasmids, which are then transfected into suitable packaging cells (e.g., HEK-293 cells). Transfected cells are then incubated with adenoviruses under conditions suitable for infection. At some frequency within the cells, homologous recombination between the vector and the virus will produce an adenoviral genome harboring the desired mutation.

Adenoviruses of the present invention can be either replication competent or replication deficient. Preferably, the adenoviral vector comprises a genome with at least one modification therein, rendering the virus replication deficient (see, e.g., International Patent Application WO 95/34671 (Kovesdi et al.)). The modification to the adenoviral genome includes, but is not limited to, addition of a DNA segment, rearrangement of a DNA segment, deletion of a DNA segment, replacement of a DNA segment, or introduction of a DNA lesion. A DNA segment can be as small as one nucleotide and as large as the adenoviral genome (e.g., about 36 kb) or, alternately, can equal the maximum amount which can be packaged into an adenoviral virion (i.e., about 38 kb). Preferred modifications to the adenoviral genome include modifications in the E1, E2, E3, and/or E4 regions. An adenovirus also preferably can be a cointegrate, i.e., a ligation of adenoviral genomic sequences with other sequences, such as other virus, phage, or plasmid sequences.

The virion and adenoviral vector of the present invention have many qualities which render them attractive choices for use in gene transfer, as well as other, applications. For example, in many embodiments, the adenovirus does not infect its native host cells as readily as does wild-type adenovirus, due to the recombinant fiber protein. Moreover, by virtue of additional modifications, such virions and vectors are less readily cleared from the host by the innate or acquired immune responses, thus boosting effective free titer and lengthening serum half-life. Furthermore, the virions and vectors have at least one non-native ligand specific for a substrate which facilitates viral propagation, targeting, purification, and/or inactivation as discussed herein. The presence of such ligands can effectively confine expression of non-native amino acids within a predefined cell type or tissue. Linking the non-native amino acid to a tissue-specific or regulable promoter further minimizes expression of the non-native amino acid outside of the targeted tissue. The ligands and the trimerization domains can be separate domains, thus permitting the virus to be easily be reengineered to incorporate different ligands without perturbing fiber trimerization.

Of course, for delivery into a host (such as an animal), a virus of the present invention can be incorporated into a suitable carrier. As such, the present invention provides a composition comprising an adenovirus of the present invention and a pharmacologically acceptable carrier (e.g., a pharmaceutically-acceptable carrier). Any suitable preparation is within the scope of the invention. The exact formulation, of course, depends on the nature of the desired application (e.g., cell type, mode of administration, etc.), and many suitable preparations are set forth in U.S. Pat. No. 5,559,099 (Wickham et al.).

Cell Line

As mentioned herein, an adenovirus of the present invention does not readily infect its native host cell via the native AR because its ability to bind ARs is significantly attenuated (due to the incorporation of the recombinant fiber protein of the present invention). Therefore, the invention provides a cell line able to propagate the inventive adenovirus. Preferably, the cell line can support viral growth for at least about 10 passages (e.g., about 15 passages), and more preferably for at least about 20 passages (e.g., about 25 passages), or even 30 or more passages.

For example, the adenoviruses can be first grown in a packaging cell line which expresses a native fiber protein gene. The resultant viral particles are therefore likely to contain both native fibers encoded by the complementing cell line and non-native fibers encoded by the adenoviral genome (such as: those fibers described herein); hence a population of such resultant viruses will contain both fiber types. Such particles will be able to bind and enter packaging cell lines via the native fiber more efficiently than particles which lack native fiber molecules. Thus, the employment of such a fiber-encoding cell line permits adenovirus genomes encoding chimeric, targeted adenovirus fibers to be grown and amplified to suitably high titers. The resultant "mixed" stocks of adenovirus produced from the cell lines encoding the native fiber molecule will contain both native and chimeric adenovirus fiber molecules; however, the particles contain genomes encoding only the chimeric adenovirus fiber. Thus, to produce a pure stock of adenoviruses having only the chimeric adenovirus fiber molecules, the "mixed" stock is used to infect a packaging cell line which does not produce native fiber (such as HEK-293 for E1-deleted non-group B viruses). The resultant adenoviruses contain only the fiber molecules encoded by the genomes (i.e., the chimeric fiber molecules).

Similar fiber-complementing cell lines have been produced and used to grow mutant adenovirus lacking the fiber gene). However, the production rates of these cell lines have generally not been great enough to produce adenovirus titers of the fiber-deleted adenovirus comparable to those of fiber-expressing adenovirus particles. The lower titers produced by such mutants can be improved by temporally regulating the expression of the native fiber to more fully complement the mutant adenovirus genome. One strategy to produce such an improved cell line is to use of a regulable promoter to permit fiber production to be controlled and activated once the cells are infected with adenovirus. Alternatively, an efficient mRNA splice site introduced into the fiber gene in the complementing cell line improves the level of fiber protein production in the cell line.

When the adenovirus is engineered to contain a ligand specific for a given cell surface binding site, any cell line expressing that receptor and capable of supporting adenoviral growth is a suitable host cell line. However, because many ligands do not bind cell surface binding sites (especially some of the novel ligands discussed herein), a cell line can be engineered to express the substrate for the ligand.

The present invention provides a cell line expressing a non-native cell-surface receptor (a pseudo-receptor) to which a virus having a ligand for said receptor binds. Any cell line capable of supporting viral growth is a suitable cell line for use in the present invention. If the virus lacks genes essential for viral replication, preferably the cell line expresses complementing levels of such gene products (see, e.g., International Patent Application WO 95/34671 (Kovesdi et al.), U.S. Pat. Nos. 5,658,724 (DeLuca) and 5,804,413 (DeLuca)). When the virus is an adenovirus, preferably the cell line of the present invention is derived from HEK-293 cells. When the virus is a herpesvirus, preferably the cell line of the present invention is derived from VERO cells.

The non-native cell surface binding site is a substrate molecule, such as described herein, to which an adenovirus having a ligand selectively binding that substrate can bind the cell and thereby promote cell entry. The binding site can recognize a non-native ligand incorporated into the adenoviral coat or a ligand native to a virus. For example, when the non-native viral ligand is a tag peptide, the binding site can be a single chain antibody (ScAb) receptor recognizing the tag. Alternatively, the ScAb can recognize an epitope present in a region of a mutated fiber knob (if present), or even an epitope present on a native adenoviral coat protein, (e.g., on the fiber, penton, hexon, etc.). Alternatively, if the non-native ligand recognizes a cell-surface substrate (e.g., membrane-bound protein), the binding site can comprise that substrate. If the substrate binding site is native to a cell-surface receptor, the cell line can express a mutant, receptor with decreased ability to interact with the cellular signal transduction pathway (e.g., a truncated receptor, such as NMDA (Li et al., *Nat. Biotech.*, 14, 989 (1996))), attenuated ability to act as an ion channel, or other modification. Infection via such modified proteins minimizes the secondary effects of viral infection on host-cell metabolism by reducing the activation of intracellular messaging pathways and their various response elements. The choice of binding site depends to a large extent on the nature of the adenovirus. However, to promote specificity of the virus for a particular cell type, the binding site preferably is not a native mammalian AR. Moreover, the binding site must be expressed on the surface of the cell to be accessible to the virus. Hence, where the binding site is a protein, it preferably has a leader sequence and a membrane tethering sequence to promote proper integration into the membrane (see, e.g., Davitz et al., *J. Exp. Med.* 163, 1150 (1986)).

The cell line can be produced by any suitable method. For example, a vector (e.g., an oligonucleotide, plasmid, viral, or other vector) containing a nucleic acid encoding the non-native receptor can be introduced into source cell line by conventional means. Preferably, the vector also encodes an agent permitting the cells harboring it to be selected (e.g., the vector can encode resistance to antibiotics which kill cells not harboring the plasmid). At some frequency, the vector will recombine with the cell genome to produce a transformed cell line expressing the non-native receptor.

EXAMPLES

While it is believed that one of skill in the art is fully able to practice the invention after reading the foregoing description, the following examples further illustrate some of its features. In particular, the examples demonstrate the construction of several recombinant fiber proteins, each exhibiting reduced affinity for native adenoviral substrates. The examples further demonstrate the inclusion of such recombinant fiber proteins into adenoviral vectors, and the retargeting of such vectors using non-native ligands. The examples also demonstrate the successful construction of a pseudoreceptor cell line able to propagate the alternatively targeted viruses. As these examples are included for purely illustrative purposes, they should not be construed to limit the scope of the invention in any respect.

The procedures employed in these examples, such as affinity chromatography, Southern blots, PCR, DNA sequencing, vector construction (including DNA extraction, isolation, restriction digestion, ligation, etc.), cell culture (including antibiotic selection), transfection of cells, protein assays (Western blotting, immunoprecipitation, immunofluorescence), etc., are techniques routinely performed by those of skill in the art (see generally Sambrook et al., *Molecular Cloning, A Laboratory Manual*, Cold Spring Harbor Laboratory, Cold Spring Harbor, N.Y. (1989)). Accordingly, in the interest of brevity, experimental protocols are not discussed in detail.

Example 1

This example describes mutant fiber trimers exhibiting reduced affinity for the CAR protein.

Using standard site-directed mutagenesis, mutations were introduced into nearly every major sheet and loop in the native Ad5 fiber knob sequence (SEQ ID NO:1). In a first series of mutagenesis, replacement mutations were designed in which between 3 and 6 contiguous amino acids within a loop were replaced by the same number of glycine residues. In a second series of mutagenesis, mutations were designed in which between 1 and 4 amino acids were deleted from the native sequence. Extensive point mutations also were conducted. One additional mutant was designed in which 12 amino acids were deleted and replaced with a tetrapeptide sequence.

Respective baculovirus clones, each containing one of the recombinant mutant protein genes, were created and used to produce recombinant mutant knob proteins in insect cells. The baculovirus-infected insect cells were freeze-thawed at 3 days post-infection to release any soluble recombinant mutant protein (approximately $10^7$ cells per ml of PBS). The freeze-thawed lysate was centrifuged and the soluble fraction and the insoluble pellet were collected. Western analysis of the soluble and insoluble fractions revealed that similar levels of the mutant and native fiber knobs were present in the soluble fraction. Mutants which retained solubility represent proteins which folded properly and trimerized, and these are set forth in Table 1. In the table, mutations are indicated by noting the location of the mutated residue or residues of the Ad5 fiber within parentheses. The identity of the native residue or residues is set forth to the left, and the identity of any substituting residue or residues is to the right of the parentheses. Deletions are further delineated using the "Δ" symbol.

TABLE 1

| Mutation Location | Mutations | |
|---|---|---|
| AB Loop (403–418) | T(404)G | RLN(412–414)GGG |
| | P(405)G | N(414)G |
| | A(406)K | A(415)G |
| | S(408)E | RLNAEK(415–417)SLNGGG |
| | S(408)G | E(416)G |
| | P(409)A | K(417)G |
| | R(412)G | K(417)L |
| B Sheet (419–428) | K(420)A | |
| C Sheet (431–440) | L(439)S | |
| CD Loop (441–453) | V(441)S | SGTVQ(449–453)GSGSG |
| | ΔSG(449–450) | |
| D Sheet (454–461) | S(454)N + R(460)Q | I(458)E + R(460)E |
| | H(456)E + R(460)E | |
| DE Loop (462–478) | D(462)A | DPE(474–476)GGG |
| | V(466)S | DPEY(474–477)GGGG |
| | L(467)S | Y(477)A |
| | NNS(469–471)GGG | Y(477)T |
| | ΔF(472) | |
| E Sheet (479–482) | N(482)A | |
| F Sheet (485–486) | L(485)G | |
| FG Loop (487–514) | E(487)G | P(505)G |
| | T(489)G | ΔK(506) |
| | A(490)G | H(506)A |
| | EGTAY(487–491)GGGGG | ΔKT(510–511) |
| | Y(491)A | SHGKTA(507–512)GSGSGS |
| | ΔTAYT(489–492) | |
| G Sheet (515–521) | N(515)S + V(517)S | Y(521)H |
| | V(517)S + Q(519)S | |
| GH Loop (522–528) | NGDKT(523–527)GSGSG | K(526)E |
| | D(525)K | K(528)S |
| | KTK(526–528)RSR | |
| H Sheet (528–536) | T(535)E | T(533)S + T(535)S |
| HI Loop (537–549) | N(537)E | GTQETGDTTPSA(538–549)GSGG |
| I Sheet (550–557) | S(551)N + S(555)N | S(553)E |
| | S(551)E | |
| IJ Loop (558–572) | SGHN(559–562)GSGS | INEI(564–567)GSGS |
| | ΔHN(561–562) | E(566)K |
| | Y(563)H | F(568)H |
| C-Terminus (573–578) | Q(580)G | E(581)G |

To determine whether a given mutant fiber had reduced affinity for CAR, competition experiments were performed by preincubating A549 cells with either the trimeric mutants or native fiber knobs followed by incubation with radiolabeled Ad5 virus. Either 1 or 10 µl volumes of the native knob preincubated with A549 cells blocked 90% or more of the labeled Ad5 binding to cells measured in the absence of a competitor. In this assay, any soluble, trimeric mutant less efficient in blocking fiber-mediated Ad5 cell binding or gene transduction than the native knob was considered to have reduced affinity for CAR. Those trimeric mutant fibers exhibiting reduced affinity for CAR in this assay are indicated in Table 2.

The trimeric mutant fiber proteins were mass produced by infecting roughly 15 million insect cells each with the baculoviral vectors (MOI=10) and culturing them for 3 days. The cells were harvested and freeze-thawed, and the cell debris was removed via centrifugation. NaCl was added to the supernatant to a final concentration of 750 ml, and then the supernatant was added to 500 µl TALON™ resin. After one hour at 25° C., the resin was centrifuged at 2,500 for two minutes. The supernatant was removed, and the resin resuspended in 10 ml 750 mM NaCl. After 30 minutes incubation, the resin suspension was run through a column. The mutant protein was eluted using 2 ml of elution fluid (20 mM TRIS, pH 8.0, 100 mM NaCl, 150 mM imidazole). The eluate was dialized once against PBS with 750 mM NaCl, once against PBS with 500 mM NaCl, and once against PBS with 250 mM NaCl. Protein concentration was determined by standard methods and protein integrity verified by Western analysis.

The purified proteins were subjected to a competition assay with Ad5 capsids to assess the degree to which each mutation decreased interaction with CAR. Serial dilutions of each mutant protein, as well as wild-type Ad5 fiber, were added to A549 cells ($10^5$ cells/well) in 24-well plates. Following this preincubation, an Ad5 vector containing the lacZ gene were added to each well (MOI=10). After a one hour incubation at 37° C., the inoculum was removed, the cells were washed with culture medium, and then and a culture medium (DMEM with 5% FCS) added. The cells were incubated overnight, lysed 18 hours post infection, and assayed for β-galactosidase activity by standard methods. Plotting the degree of β-galactosidase activity against concentration of preincubation protein permitted assessment of each protein's $IC_{50}$ value (the concentration of the competing protein at the 50% level). The degree to which each mutation reduced CAR-binding as calculated by this method is set forth in Table 2.

TABLE 2

| Mutation Number | Mutation Location | Mutation Sequence | Competition |
|---|---|---|---|
| F5K | — | Native | 100% |
| F3K | — | Native | <0.1% |
| Ad5-1 | AB Loop | S408E | <0.1% |
| Ad5-2 | AB Loop | P409A | <1% |
| Ad5-3 | AB Loop | RLNAEK(412–417)SLNGGG | <0.1% |
| Ad5-4 | AB Loop | K(417)G | <0.1% |
| Ad5-5 | B Sheet | K(420)A | <0.1% |
| Ad5-6 | DE Loop | ΔDPE(474–476) | <20% |
| Ad5-7 | DE Loop | ΔDPEY(474–477) | <0.1% |
| Ad5-8 | DE Loop | Y(477)A | <0.1% |
| Ad5-9 | FG Loop | EGTAY(487–491)GGGGG | <0.1% |
| Ad5-10 | FG Loop | ΔTAYT(489–492) | <0.1% |

Example 2

This example describes recombinant fiber proteins exhibiting reduced affinity for the CAR protein.

The Ad9 and long Ad41 fiber proteins corresponding to mutations Ad5-1, Ad5-2, Ad5-4, Ad5-5, and Ad5-9 (see FIG. 1) were generated. The resultant mutant proteins were soluble, and each was used in competition assays against wild type Ad5, as described in Example 1, to assess whether the mutations affected CAR binding. The results of these experiments (presented in Table 3) reveal that residues important for CAR binding are conserved among adenoviral serotypes.

TABLE 3

| Mutation | Mutation Sequence | Corresponding Ad5 Mutation | Competition |
|---|---|---|---|
| Ad9-1 | S(189)E | Ad5-1 | No |
| Ad9-2 | P(190)A | Ad5-2 | No |
| Ad9-3 | K(198)G | Ad5-4 | No |
| Ad9-4 | K(201)A | Ad5-5 | No |
| Ad9-5 | Y(262)A | Ad5-8 | No |
| Ad41-1 | S(395)E | Ad5-1 | No |
| Ad41-2 | P(369)A | Ad5-2 | No |
| Ad41-3 | L(404)G | Ad5-4 | No |
| Ad41-3 | T(470)A | Ad5-8 | No |

Example 3

This example describes the production of a pseudo-receptor for constructing a cell line able to replicate adenoviruses lacking native cell-binding function (but targeted for the pseudo-receptor). Specifically, the exemplary pseudo-receptor includes a binding domain from a single-chain antibody recognizing HA.

Anti-HA ScFv was constructed as an N-Term-VL-VH fusion protein. RT-PCR was performed on RNA obtained from hybridomas producing HA antibodies using primers specific for κ- or γ2β- and C-terminus of the VL and VH genes (see Gilliland et al., Tissue Antigens, 47, 1–20 (1996)). After sequencing the resulting PCR products, specific oligonucleotides were designed to amplify the VL-VH fusion in a second round of PCR. The final PCR product was cloned to create a plasmid for production of anti-HA ScFv in E. coli. The expressed protein has a C-terminal E peptide for detection of binding to HA-tagged penton base via Western analysis of ELISA assay. Upon transformation of bacterial cells with the plasmid. Western analysis using an antibody recognizing the E peptide revealed a protein of the expected size.

To determine whether the anti-HA ScFv was functional, it was used in protein A immunoprecipitation assays using adenoviral coat proteins (recombinant penton base) containing the HA epitope. The anti-HA ScFv was able to precipitate HA-containing penton base proteins. These results indicate the successful construction of the extracellular portion of a pseudo-receptor for binding an adenovirus having a non-native ligand (i.e., HA).

To create an entire anti-HA pseudo-receptor, the anti-HA ScFv was cloned in frame with sequences encoding a C-terminal pair of myc epitopes followed by the PDGF receptor transmembrane anchor. The entire sequence of this pseudo-receptor is indicated at SEQ ID NO:28. A eukaryotic expression plasmid containing this sequence, pSc(HA), was transfected into HEK-293 cells. The following day the pSc(HA)-transfected cells or cells transfected with a control ScFv construct were incubated for 30 min on ice with a fluoroscein-tagged HA peptide (HA*) or with a fluoroscein-tagged scrambled HA peptide (scrHA*). Following the incubation of HA* with the pSc(HA)-transfected cells, a discrete population of cells was found to brightly fluoresce specifically around the cell membrane. The pSc(HA)-transfected cells incubated with the scrHA* peptide did not display this fluorescent pattern, nor did the cells transfected with the control plasmid and then incubated with HA*. Enhanced fluorescence of the pSc(HA)-transfected cells incubated with HA* was also demonstrated by FACS analysis. Moreover, preincubation of the anti-HA pseudo-receptor cells with excess unlabelled HA peptide, but not unlabelled FLAG peptide, blocked the fluorescent pattern observed on cells incubated with HA* alone.

These results demonstrate the successful construction and expression of a cell line consisting essentially of cells expressing a functional pseudo-receptor.

Example 4

This example describes an alternatively targeted adenovirus having recombinant fiber proteins exhibiting reduced affinity for the CAR protein and having a non-native ligand.

The Ad5-10 mutant described in Example 1 was subjected to further site directed mutagenesis to introduce a polypeptide including the HA epitope into the HI loop of the fiber knob (between amino acids 543 and 544 of SEQ ID NO:1). The resultant fiber has the TAYT deletion in the FG loop and an HA epitope sequence inserted into the HI loop.

The gene encoding this mutant fiber was combined into a plasmid that contains a full length, E1- and E3-deleted adenovirus genome carrying the above fiber mutation plus a CMV-driven LacZ reporter gene in the E1 region. This plasmid was then linearized and transfected into HEK-293 cells expressing the anti-HA pseudo-receptor described in Example 3. After 5 days the cells were freeze-thawed three times, and the virus-containing lysate was passaged onto fresh anti-HA-293 cells.

The resultant adenoviruses were further amplified in the anti-HA-293 cells and then purified using standard methods. The vector (AdZ.F*fg(HA)hi) exhibits reduced binding capacity to CAR on standard HEK-293 cells due to the TAYT deletion; however, it binds with high affinity via its HA epitope to the anti-HA pseudoreceptor present on the anti-HA-293 cell line.

Example 5

This example describes an alternatively targeted adenovirus having recombinant fiber proteins exhibiting reduced affinity for the CAR protein and having more than one non-native ligand.

The Ad5-10 mutant described in Example 1 was subjected to further site directed mutagenesis to introduce a polypeptide including the HA epitope and a high affinity RGD ligand into the HI loop of the fiber knob (between amino acids 543 and 544 of SEQ ID NO:1). The resultant plasmid encodes a fiber with the TAYT deletion in the FG loop and an RGD sequence inserted into the HI loop.

The gene encoding this mutant fiber gene was then combined into a plasmid that contains a full length, E1 and E3-deleted adenovirus genome carrying the above fiber mutation plus a CMV-driven LacZ reporter gene in the E1 region. This plasmid was then linearized and transfected into HEK-293 cells expressing the anti-HA pseudo-receptor described in Example 2. After 5 days the cells are freeze-thawed three times and the virus-containing lysate is passaged onto fresh HEK-293 cells.

The resultant adenoviruses were further amplified in the anti-HA-293 cells and then purified using standard methods. The vector exhibits reduced binding capacity to CAR on standard HEK-293 cells due to the TAYT deletion; however, it efficiently infects cells expressing $\alpha_v$ integrins (such as tumor cells) via the RGD ligand present in the HI loop.

Example 6

This example describes an alternatively targeted adenovirus having recombinant fiber proteins exhibiting reduced affinity for the CAR protein and having a non-native ligand.

The Ad5-3 mutant described in Example 1 was subjected to further site directed mutagenesis to introduce an 18 amino acid polypeptide including the HA epitope into the HI loop of the fiber knob (between amino acids 543 and 544 of SEQ ID NO:1). The resultant fiber has the RLNAEK mutation of the AB loop and an HA epitope sequence inserted into the HI loop.

The gene encoding this mutant fiber was combined into a plasmid that contains a full length, E1- and E3-deleted adenovirus genome carrying the above fiber mutation plus a CMV-driven LacZ reporter gene in the E1 region. This plasmid was then linearized and transfected into HEK-293 cells expressing the anti-HA pseudo-receptor described in Example 3. After 5 days the cells were freeze-thawed three times, and the virus-containing lysate was passaged onto fresh anti-HA 293 cells.

The resultant adenoviruses were further amplified in the anti-HA 293 cells and then purified using standard methods. The vector (AdZ.F*ab(HA)hi) exhibits reduced binding capacity to CAR on standard HEK-293 cells due to the RLNAEK mutation; however, it binds with high affinity via its HA epitope to the anti-HA pseudoreceptor present on the anti-HA 293 cell line.

Example 7

This example describes an alternatively targeted adenovirus having recombinant fiber proteins exhibiting reduced affinity for the CAR protein and having more than one non-native ligand.

The Ad5-3 mutant described in Example 1 was subjected to further site directed mutagenesis to introduce a polypeptide including the HA epitope and a high affinity RGD ligand into the HI loop of the fiber knob (between amino acids 543 and 544 of SEQ ID NO:1). The resultant plasmid encodes a fiber with the RLNAEK mutation of the AB loop and an HA epitope and RGD sequence inserted into the HI loop.

The gene encoding this mutant fiber gene was then combined into a plasmid that contains a full length, E1- and E3-deleted adenovirus genome carrying the above fiber mutation plus a CMV-driven LacZ reporter gene in the E1 region. This plasmid was then linearized and transfected into HEK-293 cells expressing the anti-HA pseudo-receptor described in Example 3. After 5 days the cells are freeze-thawed three times, and the virus-containing lysate was passaged onto fresh anti-HA 293 cells.

The resultant adenoviruses were further amplified in the anti-HA 293 cells and then purified using standard methods. The vector exhibits reduced binding capacity to CAR on standard HEK-293 cells due to the RLNAEK mutation; however, it binds with high affinity via its HA epitope to the anti-HA pseudoreceptor present on the anti-HA 293 cell line. Moreover, the virus also efficiently infects cells expressing $\alpha_v$ integrins (such as tumor cells) via the RGD ligand present in the HI loop.

Example 8

This example describes an alternatively targeted adenovirus having recombinant fiber proteins exhibiting reduced affinity for the CAR protein and having a non-native ligand.

A mutation was introduced into the Ad2 fiber knob, deleting the Asn-Pro residues in the FG loop (residues 90 and 91 of SEQ ID NO:7). Additionally, the high-affinity RGD motif was introduced into the HI loop of this protein. The sequences encoding the knob domain were fused to sequences encoding the Ad5 shaft, resulting in a nucleic acid encoding a chimeric Ad5-Ad2 fiber. This construct was cloned into an Ad5 genome also containing the lacZ gene (the Adz virus), replacing the native fiber sequence. The resultant viruses are termed AdZ.F*(RGD).

Increasing particle doses of either AdZ or AdZ.F*(RGD) were incubated with either SKOV-3 cells (which express both CAR and $\alpha_v$ integrins) or Ramos cells (which express CAR but not $\alpha_v$ integrins) in suspension ($10^6$ cells/300 µl medium) for one hour at 36° C., following which the cells were washed and incubated overnight. Following the incubation, the cells were assayed for lacZ activity using conventional methods.

The SKOV-3 cells were transduced by both viruses, while the Ramos cells were transuded by AdZ, but only poorly transduced by AdZ.F*(RGD). These results demonstrate that the native CAR-binding ability of the vector can be blocked by mutating selective residues of the fiber knob and the virus retarded by the addition of a non-native ligand to the viral coat protein.

Example 9

This example demonstrated the reduced affinity for the CAR protein of recombinant fiber proteins.

Various cell types (A172, HuVEC, HCAEC, A549, HeLa, HEK-293, and HS68) ($10^6$ cells/300 µl medium) were preincubated for 30 minutes at 37° C. with either soluble Ad5 fiber protein (3 µg/ml) or penton base protein (100 µg/ml). Following this incubation, either AdZ, AdZ.F*ab(HA)hi or AdZ.F*fg(HA)hi (100 viral particles/cell) were added to the cells. After a one hour incubation at 37° C., the cells were twice washed and incubated overnight, again at 37° C. Following the incubation, the cells were assayed for lacZ activity using conventional methods. Except for the HS68 fibroblast cell line. the results indicate that preincubation with Ad5 fiber blocked AdZ transduction, but preincubation with penton base did not. In contrast, the viruses containing the mutant fibers were not blocked by preincubation with fiber, but were blocked by preincubation with penton base. These data are consistent with the ablation of native fiber-based infection through mutating the fibers as indicated.

Example 10

This example demonstrated the alteration of viral targeting in vivo, using an alternatively targeted adenovirus.

The jugular veins of Balb/C mice were injected with either Adz, AdZ.F*ab(HA)hi or AdZ.F*fg(HA)hi ($10^{10}$ particles/animal in 100 ml, eight animals each). The experiments were run in duplicate. and two animals served as a control (100 ml saline). At one day post inoculation, the animals were sacrificed and the liver of each was snap-frozen in liquid nitrogen. The livers were then pulverized, and lacZ activity was assayed by conventional methods to determine enzymatic activity/mass of tissue.

The livers from the AdZ.F*ab(HA)hi- or AdZ.F*fg(HA)hi-inoculated animals exhibited about 10% of the lacZ activity as those inoculated with AdZ, while control animals exhibited background levels of activity. These results indicate that fiber mutations ablating native cell-receptor binding are effective in greatly reducing native tropism in vivo.

All references cited herein are hereby incorporated by reference to the same extent as if each reference were individually and specifically indicated to be incorporated by reference and were set forth in its entirety herein.

While this invention has been described with an emphasis on preferred embodiments, it will be obvious to those of ordinary skill in the art that variations of the preferred embodiments can be used and that it is intended that the invention can be practiced otherwise than as specifically described herein. Accordingly, this invention includes all modifications encompassed within the spirit and scope of the invention as defined by the following claims.

What is claimed is:

1. A recombinant fiber protein that interacts with an adenoviral penton base and comprises a trimerization domain, wherein said trimerization domain comprises an adenoviral fiber knob domain having a mutation or a deletion of at least one amino acid residue within a region selected from the group consisting of the AB loop, B sheet, DE loop, and FG loop of a wild-type Ad5 fiber protein, and corresponding regions of wild-type fiber proteins of other adenovirus serotypes, wherein said trimerization domain does not comprise a ligand, and wherein said recombinant fiber protein trimerizes when produced in a eukaryotic cell.

2. A recombinant fiber protein that interacts with an adenoviral penton base and comprises a trimerization domain, wherein said trimerization domain comprises an adenoviral fiber knob domain having a mutation or a deletion of at least one amino acid residue selected from the group consisting of residues 404, 405, 406, 408, 409, 412, 413, 414, 415, 416, 417, 420, 439, 441, 442, 449, 450, 451, 452, 453, 454, 456, 458, 460, 462, 466, 467, 469, 470, 471, 472, 474, 475, 476, 477, 482, 485, 487, 488, 489, 490, 491, 492, 505, 506, 507, 508, 509, 510, 511, 512, 515, 517, 519, 521, 522, 523, 524, 525, 526, 527, 528, 533, 535, 537, 538, 539, 540, 541, 542, 543, 544, 545, 546, 547, 548, 549, 551, 553, 555, 559, 560, 561, 562, 563, 564, 565, 566, 567, 568, 580, and 581 of a wild-type Ad5 fiber protein, and corresponding residues of wild-type fiber proteins of other adenovirus serotypes, wherein said trimerization domain does not comprise a ligand, and wherein said recombinant fiber protein trimerizes when produced in a eukaryotic cell.

3. The recombinant fiber protein of claim 1, wherein the recombinant fiber protein comprises an amino terminus of an adenoviral fiber protein.

4. The recombinant fiber protein of claim 3, wherein said region is the AB loop.

5. The recombinant fiber protein of claim 3, wherein said region is the B sheet.

6. The recombinant fiber protein of claim 3, wherein said amino acid residue is selected from the group consisting of residues 408, 409, 412, 413, 414, 415, 416, 417, 420, 474, 475, 476, 477, 487, 488, 489, 490, 491, and 492 of the wild-type Ad5 fiber protein.

7. The recombinant fiber protein of claim 3, wherein said adenoviral fiber knob domain has a mutation that alters the charge of said amino acid residue.

8. A trimer comprising the recombinant fiber protein of claim 3, wherein said trimer has an affinity for a native adenoviral cellular receptor of at least an order of magnitude less than a wild-type adenoviral fiber trimer.

9. An adenoviral virion comprising the trimer of claim 8.

10. The adenoviral virion of claim 9, comprising a penton base having a mutation or a deletion of at least one native RGD sequence.

11. The adenoviral virion of claim 9, comprising a hexon having a mutation or a deletion of at least one native HVR sequence.

12. The adenoviral virion of claim 9, wherein the recombinant fiber protein lacks one or more native glycosylation or phosphorylation sites.

13. The adenoviral virion of claim 9, which is conjugated to a lipid derivative of polyethylene glycol comprising a primary amine group, an epoxy group, or a diacylglycerol group.

14. The adenoviral virion of claim 9, which elicits less immunogenicity in a host animal than does a wild-type adenovirus.

15. The adenoviral virion of claim 9, comprising a non-adenoviral ligand.

16. The adenoviral virion of claim 15, wherein said non-adenoviral ligand is conjugated to a fiber.

17. The adenoviral virion of claim 15, wherein said non-adenoviral ligand is conjugated to a penton.

18. The adenoviral virion of claim 15, wherein said non-adenoviral ligand is conjugated to a hexon.

19. The adenoviral virion of claim 15, wherein said non-adenoviral ligand binds a substrate other than a native mammalian adenoviral receptor.

20. The adenoviral virion of any of claim 15, wherein said non-adenoviral ligand binds a substrate other than a native cell-surface protein.

21. The adenoviral virion of claim 20, wherein said substrate is present on the surface of a cell.

22. An adenoviral vector comprising the adenoviral virion of claim 9 and an adenoviral genome.

23. The adenoviral vector of claim 22, which is replication incompetent.

24. The adenoviral vector of claim 22, which does not productively infect HEK-293 cells.

25. The adenoviral vector of claim 22, wherein said virion comprises a non-adenoviral ligand, and said adenoviral genome comprises a non-native nucleic acid for transcription.

26. The adenoviral vector of claim 25, wherein said non-native nucleic acid for transcription is operably linked to a non-adenoviral promoter.

27. The adenoviral vector of claim 26, wherein said ligand binds to a substrate present on the surface of a cell and wherein said non-adenoviral promoter is active within said cell.

28. The adenoviral vector of claim 26, wherein said non-adenoviral promoter is a tissue-specific promoter.

29. The adenoviral vector of claim 26, wherein said non-adenoviral promoter is a regulable promoter.

30. A method of infecting a cell, comprising contacting a cell with an adenoviral vector of claim 22.

31. The method of claim 30, wherein said adenoviral genome comprises a non-native nucleic acid encoding a protein, and wherein said nucleic acid is expressed within said cell to produce said protein.

32. The recombinant fiber protein of claim 2, wherein the recombinant fiber protein comprises an amino terminus of an adenoviral fiber protein.

33. The recombinant fiber protein of claim 32, wherein said amino acid residue is selected from the group consisting of residues 189, 190, 198, 201, and 262 of the native Ad9 fiber protein.

34. The recombinant fiber protein of claim 32, wherein said amino acid residue is selected from the group consisting of residues 395, 396, 404, 407, and 470 of the native Ad41 long fiber protein.

35. The recombinant fiber protein of claim 32, wherein said amino acid residue is selected from the group consisting of residues 136, 155, 177, 181, 198, 210, 211, 215, 233, 234, 236, 238, 248, 257, 260, 261, 276, 284, 302, 303, 317, and 318 of the native Ad3 fiber protein.

36. The recombinant fiber protein of claim 32, wherein said adenoviral fiber knob domain has a mutation that alters the charge of said residue.

37. A trimer comprising the recombinant fiber protein of claim 32, wherein said trimer has an affinity for a native adenoviral cellular receptor of at least an order of magnitude less than a wild-type adenoviral fiber trimer.

38. An adenoviral virion comprising the trimer of claim 37.

39. The adenoviral virion of claim 38, comprising a penton base having a mutation or a deletion of at least one native RGD sequence.

40. The adenoviral virion of claim 38, comprising a hexon having a mutation or a deletion of at least one native HVR sequence.

41. The adenoviral virion of claim 38, wherein the recombinant fiber protein lacks one or more native glycosylation or phosphorylation sites.

42. The adenoviral virion of claim 38, which is conjugated to a lipid derivative of polyethylene glycol comprising a primary amine group, an epoxy group, or a diacylglycerol group.

43. The adenoviral virion of claim 38, which elicits less immunogenicity in a host animal than does a wild-type adenovirus.

44. The adenoviral virion of claim 38, comprising a non-adenoviral ligand.

45. The adenoviral virion of claim 44, wherein said non-adenoviral ligand is conjugated to a fiber.

46. The adenoviral virion of claim 44, wherein said non-adenoviral ligand is conjugated to a penton.

47. The adenoviral virion of claim 44, wherein said non-adenoviral ligand is conjugated to a hexon.

48. The adenoviral virion of claim 44, wherein said non-adenoviral ligand binds a substrate other than a native mammalian adenoviral receptor.

49. The adenoviral virion of any of claim 44, wherein said non-adenoviral ligand binds a substrate other than a native cell-surface protein.

50. The adenoviral virion of claim 49, wherein said substrate is present on the surface of a cell.

51. An adenoviral vector comprising the adenoviral virion of claim 38 and an adenoviral genome.

52. The adenoviral vector of claim 51, which is replication incompetent.

53. The adenoviral vector of claim 51, which does not productively infect HEK-293 cells.

54. The adenoviral vector of claim 51, wherein said virion comprises a non-adenoviral ligand, and said adenoviral genome comprises a non-native nucleic acid for transcription.

55. The adenoviral vector of claim 54, wherein said non-native nucleic acid for transcription is operably linked to a non-adenoviral promoter.

56. The adenoviral vector of claim 55, wherein said ligand binds to a substrate present on the surface of a cell and wherein said non-adenoviral promoter is active within said cell.

57. The adenoviral vector of claim 55, wherein said non-adenoviral promoter is a tissue-specific promoter.

58. The adenoviral vector of claim 56, wherein said non-adenoviral promoter is a regulable promoter.

59. A method of infecting a cell, comprising contacting a cell with an adenoviral vector of claim 51.

60. The method of claim 59, wherein said adenoviral genome comprises a non-native nucleic acid encoding a protein, and wherein said nucleic acid is expressed within said cell to produce said protein.

* * * * *

SEQUENCE LISTING

```
<160> NUMBER OF SEQ ID NOS: 32

<210> SEQ ID NO 1
<211> LENGTH: 581
<212> TYPE: PRT
<213> ORGANISM: Human adenovirus serotype 5

<400> SEQUENCE: 1

Met Lys Arg Ala Arg Pro Ser Glu Asp Thr Phe Asn Pro Val Tyr Pro
1               5                   10                  15

Tyr Asp Thr Glu Thr Gly Pro Pro Thr Val Pro Phe Leu Thr Pro Pro
            20                  25                  30

Phe Val Ser Pro Asn Gly Phe Gln Glu Ser Pro Pro Gly Val Leu Ser
        35                  40                  45

Leu Arg Leu Ser Glu Pro Leu Val Thr Ser Asn Gly Met Leu Ala Leu
    50                  55                  60
```

-continued

```
Lys Met Gly Asn Gly Leu Ser Leu Asp Glu Ala Gly Asn Leu Thr Ser
 65                  70                  75                  80

Gln Asn Val Thr Thr Val Ser Pro Pro Leu Lys Lys Thr Lys Ser Asn
                 85                  90                  95

Ile Asn Leu Glu Ile Ser Ala Pro Leu Thr Val Thr Ser Glu Ala Leu
            100                 105                 110

Thr Val Ala Ala Ala Ala Pro Leu Met Val Ala Gly Asn Thr Leu Thr
        115                 120                 125

Met Gln Ser Gln Ala Pro Leu Thr Val His Asp Ser Lys Leu Ser Ile
    130                 135                 140

Ala Thr Gln Gly Pro Leu Thr Val Ser Glu Gly Lys Leu Ala Leu Gln
145                 150                 155                 160

Thr Ser Gly Pro Leu Thr Thr Thr Asp Ser Thr Leu Thr Ile Thr
                165                 170                 175

Ala Ser Pro Pro Leu Thr Thr Ala Thr Gly Ser Leu Gly Ile Asp Leu
                180                 185                 190

Lys Glu Pro Ile Tyr Thr Gln Asn Gly Lys Leu Gly Leu Lys Tyr Gly
                195                 200                 205

Ala Pro Leu His Val Thr Asp Asp Leu Asn Thr Leu Thr Val Ala Thr
    210                 215                 220

Gly Pro Gly Val Thr Ile Asn Asn Thr Ser Leu Gln Thr Lys Val Thr
225                 230                 235                 240

Gly Ala Leu Gly Phe Asp Ser Gln Gly Asn Met Gln Leu Asn Val Ala
                245                 250                 255

Gly Gly Leu Arg Ile Asp Ser Gln Asn Arg Arg Leu Ile Leu Asp Val
                260                 265                 270

Ser Tyr Pro Phe Asp Ala Gln Asn Gln Leu Asn Leu Arg Leu Gly Gln
                275                 280                 285

Gly Pro Leu Phe Ile Asn Ser Ala His Asn Leu Asp Ile Asn Tyr Asn
                290                 295                 300

Lys Gly Leu Tyr Leu Phe Thr Ala Ser Asn Asn Ser Lys Lys Leu Glu
305                 310                 315                 320

Val Asn Leu Ser Thr Ala Lys Gly Leu Met Phe Asp Ala Thr Ala Ile
                325                 330                 335

Ala Ile Asn Ala Gly Asp Gly Leu Glu Phe Gly Ser Pro Asn Ala Pro
            340                 345                 350

Asn Thr Asn Pro Leu Lys Thr Lys Ile Gly His Gly Leu Glu Phe Asp
            355                 360                 365

Ser Asn Lys Ala Met Val Pro Lys Leu Gly Thr Gly Leu Ser Phe Asp
    370                 375                 380

Ser Thr Gly Ala Ile Thr Val Gly Asn Lys Asn Asn Asp Lys Leu Thr
385                 390                 395                 400

Leu Trp Thr Thr Pro Ala Pro Ser Pro Asn Cys Arg Leu Asn Ala Glu
                405                 410                 415

Lys Asp Ala Lys Leu Thr Leu Val Leu Thr Lys Cys Gly Ser Gln Ile
            420                 425                 430

Leu Ala Thr Val Ser Val Leu Ala Val Lys Gly Ser Leu Ala Pro Ile
        435                 440                 445

Ser Gly Thr Val Gln Ser Ala His Leu Ile Ile Arg Phe Asp Glu Asn
    450                 455                 460

Gly Val Leu Leu Asn Asn Ser Phe Leu Asp Pro Glu Tyr Trp Asn Phe
465                 470                 475                 480

Arg Asn Gly Asp Leu Thr Glu Gly Thr Ala Tyr Thr Asn Ala Val Gly
```

```
                    485                 490                 495
Phe Met Pro Asn Leu Ser Ala Tyr Pro Lys Ser His Gly Lys Thr Ala
            500                 505                 510

Lys Ser Asn Ile Val Ser Gln Val Tyr Leu Asn Gly Asp Lys Thr Lys
            515                 520                 525

Pro Val Thr Leu Thr Ile Thr Leu Asn Gly Thr Gln Glu Thr Gly Asp
            530                 535                 540

Thr Thr Pro Ser Ala Tyr Ser Met Ser Phe Ser Trp Asp Trp Ser Gly
545                 550                 555                 560

His Asn Tyr Ile Asn Glu Ile Phe Ala Thr Ser Ser Tyr Thr Phe Ser
                565                 570                 575

Tyr Ile Ala Gln Glu
            580

<210> SEQ ID NO 2
<211> LENGTH: 562
<212> TYPE: PRT
<213> ORGANISM: Human adenovirus serotype 41.LONG

<400> SEQUENCE: 2

Met Lys Arg Ala Arg Leu Glu Asp Asp Phe Asn Pro Val Tyr Pro Tyr
1               5                   10                  15

Glu His Tyr Asn Pro Leu Asp Ile Pro Phe Ile Thr Pro Pro Phe Ala
                20                  25                  30

Ser Ser Asn Gly Leu Gln Glu Lys Pro Pro Gly Val Leu Ser Leu Lys
            35                  40                  45

Tyr Thr Asp Pro Leu Thr Thr Lys Asn Gly Ala Leu Thr Leu Lys Leu
        50                  55                  60

Gly Thr Gly Leu Asn Ile Asp Glu Asn Gly Asp Leu Ser Ser Asp Ala
65                  70                  75                  80

Ser Val Glu Val Ser Ala Pro Ile Thr Lys Thr Asn Lys Ile Val Gly
                85                  90                  95

Leu Asn Tyr Thr Lys Pro Leu Ala Leu Arg Ser Asn Ala Leu Thr Leu
                100                 105                 110

Ser Tyr Asn Ala Pro Leu Asn Val Val Asn Asn Leu Ala Leu Asn
            115                 120                 125

Ile Ser Gln Pro Val Thr Val Asn Ala Asn Asn Glu Leu Ser Leu Leu
        130                 135                 140

Ile Asp Ala Pro Leu Asn Ala Asp Thr Gly Thr Leu Arg Leu Gln Ser
145                 150                 155                 160

Ala Ala Pro Leu Gly Leu Val Asp Lys Thr Leu Lys Val Leu Phe Ser
                165                 170                 175

Ser Pro Leu Tyr Leu Asp Asn Asn Phe Leu Thr Leu Ala Ile Glu Arg
            180                 185                 190

Pro Leu Ala Leu Ser Ser Ser Arg Ala Val Thr Leu Lys Tyr Ser Pro
        195                 200                 205

Pro Leu Lys Ile Glu Asn Glu Asn Leu Thr Leu Ser Thr Gly Gly Pro
    210                 215                 220

Phe Thr Val Ser Gly Gly Asn Leu Asn Leu Thr Thr Ser Ala Pro Leu
225                 230                 235                 240

Ser Val Gln Asn Asn Ser Leu Ser Leu Val Ile Thr Ser Pro Leu Lys
                245                 250                 255

Val Ile Asn Ser Met Leu Ala Val Gly Val Asn Pro Pro Phe Thr Ile
            260                 265                 270
```

```
Thr Asp Ser Gly Leu Ala Met Asp Leu Gly Asp Gly Leu Ala Leu Gly
        275                 280                 285

Gly Ser Lys Leu Ile Ile Asn Leu Gly Pro Gly Leu Gln Met Ser Asn
        290                 295                 300

Gly Ala Ile Thr Leu Ala Leu Asp Ala Ala Leu Pro Leu Gln Tyr Arg
305                 310                 315                 320

Asp Asn Gln Leu Gln Leu Arg Ile Gly Ser Thr Ser Gly Leu Ile Met
                325                 330                 335

Ser Gly Val Thr Gln Thr Leu Asn Val Asn Ala Asn Thr Gly Lys Gly
            340                 345                 350

Leu Ala Val Glu Asn Asn Ser Leu Val Val Lys Leu Gly Asn Gly Leu
        355                 360                 365

Arg Phe Asp Ser Trp Gly Ser Ile Thr Val Ser Pro Thr Thr Thr Thr
    370                 375                 380

Pro Thr Thr Leu Trp Thr Thr Ala Asp Pro Ser Pro Asn Ala Thr Phe
385                 390                 395                 400

Tyr Glu Ser Leu Asp Ala Lys Val Trp Leu Val Leu Lys Cys Asn
                405                 410                 415

Gly Met Val Asn Gly Thr Ile Ser Ile Lys Ala Gln Lys Gly Ile Leu
                420                 425                 430

Leu Arg Pro Thr Ala Ser Phe Ile Ser Phe Val Met Tyr Phe Tyr Ser
        435                 440                 445

Asp Gly Thr Trp Arg Lys Asn Tyr Pro Val Phe Asp Asn Glu Gly Ile
    450                 455                 460

Leu Ala Asn Ser Ala Thr Trp Gly Tyr Arg Gln Gly Gln Ser Ala Asn
465                 470                 475                 480

Thr Asn Val Ser Asn Ala Val Glu Phe Met Pro Ser Ser Lys Arg Tyr
                485                 490                 495

Pro Asn Gln Lys Gly Ser Glu Val Gln Asn Met Ala Leu Thr Tyr Thr
            500                 505                 510

Phe Leu Gln Gly Asp Pro Asn Met Ala Ile Ser Phe Gln Ser Ile Tyr
        515                 520                 525

Asn His Ala Leu Glu Gly Tyr Ser Leu Lys Phe Thr Trp Arg Val Arg
    530                 535                 540

Asn Asn Glu Arg Phe Asp Ile Pro Cys Cys Ser Phe Ser Tyr Val Thr
545                 550                 555                 560

Glu Gln

<210> SEQ ID NO 3
<211> LENGTH: 362
<212> TYPE: PRT
<213> ORGANISM: Human adenovirus serotype 9

<400> SEQUENCE: 3

Met Ser Lys Arg Leu Arg Val Glu Asp Asp Phe Asn Pro Val Tyr Pro
1               5                   10                  15

Tyr Gly Tyr Ala Arg Asn Gln Asn Ile Pro Phe Leu Thr Pro Pro Phe
            20                  25                  30

Val Ser Ser Asp Gly Phe Gln Asn Phe Pro Pro Gly Val Leu Ser Leu
        35                  40                  45

Lys Leu Ala Asp Pro Ile Ala Ile Val Asn Gly Asn Val Ser Leu Lys
    50                  55                  60

Val Gly Gly Gly Leu Thr Leu Gln Asp Gly Thr Gly Lys Leu Thr Val
65                  70                  75                  80
```

-continued

Asn Ala Asp Pro Pro Leu Gln Leu Thr Asn Asn Lys Leu Gly Ile Ala
              85                  90                  95

Leu Asp Ala Pro Phe Asp Val Ile Asp Asn Lys Leu Thr Leu Leu Ala
            100                 105                 110

Gly His Gly Leu Ser Ile Ile Thr Lys Glu Thr Ser Thr Leu Pro Gly
            115                 120                 125

Leu Arg Asn Thr Leu Val Val Leu Thr Gly Lys Gly Ile Gly Thr Glu
        130                 135                 140

Ser Thr Asp Asn Gly Gly Thr Val Cys Val Arg Val Gly Glu Gly Gly
145                 150                 155                 160

Gly Leu Ser Phe Asn Asn Asp Gly Asp Leu Val Ala Phe Asn Lys Lys
                165                 170                 175

Glu Asp Lys Arg Thr Leu Trp Thr Thr Pro Asp Thr Ser Pro Asn Cys
            180                 185                 190

Lys Ile Asp Gln Asp Lys Asp Ser Lys Leu Thr Leu Val Leu Thr Lys
        195                 200                 205

Cys Gly Ser Gln Ile Leu Ala Asn Val Ser Leu Ile Val Val Asp Gly
    210                 215                 220

Lys Tyr Lys Ile Ile Asn Asn Thr Gln Pro Ala Leu Lys Gly Phe
225                 230                 235                 240

Thr Ile Lys Leu Leu Phe Asp Glu Asn Gly Val Leu Met Glu Ser Ser
                245                 250                 255

Asn Leu Gly Lys Ser Tyr Trp Asn Phe Arg Asn Glu Asn Ser Ile Met
            260                 265                 270

Ser Thr Ala Tyr Glu Lys Ala Ile Gly Phe Met Pro Asn Leu Val Ala
        275                 280                 285

Tyr Pro Lys Pro Thr Ala Gly Ser Lys Lys Tyr Ala Arg Asp Ile Val
    290                 295                 300

Tyr Gly Asn Ile Tyr Leu Gly Gly Lys Pro Asp Gln Pro Val Thr Ile
305                 310                 315                 320

Lys Thr Thr Phe Asn Gln Glu Thr Gly Cys Glu Tyr Ser Ile Thr Phe
                325                 330                 335

Asp Phe Ser Trp Ala Lys Thr Tyr Val Asn Val Glu Phe Glu Thr Thr
            340                 345                 350

Ser Phe Thr Phe Ser Tyr Ile Ala Gln Glu
        355                 360

<210> SEQ ID NO 4
<211> LENGTH: 319
<212> TYPE: PRT
<213> ORGANISM: Human adenovirus serotype 3

<400> SEQUENCE: 4

Met Ala Lys Arg Ala Arg Leu Ser Thr Ser Phe Asn Pro Val Tyr Pro
1               5                   10                  15

Tyr Glu Asp Glu Ser Ser Ser Gln His Pro Phe Ile Asn Pro Gly Phe
            20                  25                  30

Ile Ser Pro Asp Gly Phe Thr Gln Ser Pro Asn Gly Val Leu Ser Leu
        35                  40                  45

Lys Cys Val Asn Pro Leu Thr Thr Ala Ser Gly Ser Leu Gln Leu Lys
    50                  55                  60

Val Gly Ser Gly Leu Thr Val Asp Thr Thr Asp Gly Ser Leu Glu Glu
65                  70                  75                  80

Asn Ile Lys Val Asn Thr Pro Leu Thr Lys Ser Asn His Ser Ile Asn
                85                  90                  95

```
Leu Pro Ile Gly Asn Gly Leu Gln Ile Glu Gln Asn Lys Leu Cys Ser
                100                 105                 110

Lys Leu Gly Asn Gly Leu Thr Phe Asp Ser Ser Asn Ser Ile Ala Leu
            115                 120                 125

Lys Asn Asn Thr Leu Trp Thr Gly Pro Lys Pro Glu Ala Asn Cys Ile
130                 135                 140

Ile Glu Tyr Gly Lys Gln Asn Pro Asp Ser Lys Leu Thr Leu Ile Leu
145                 150                 155                 160

Val Lys Asn Gly Gly Ile Val Asn Gly Tyr Val Thr Leu Met Gly Ala
                165                 170                 175

Ser Asp Tyr Val Asn Thr Leu Phe Lys Asn Lys Asn Val Ser Ile Asn
            180                 185                 190

Val Glu Leu Tyr Phe Asp Ala Thr Gly His Ile Leu Pro Asp Ser Ser
        195                 200                 205

Ser Leu Lys Thr Asp Leu Glu Leu Lys Tyr Lys Gln Thr Ala Asp Phe
210                 215                 220

Ser Ala Arg Gly Phe Met Pro Ser Thr Thr Ala Tyr Pro Phe Val Leu
225                 230                 235                 240

Pro Asn Ala Gly Thr His Asn Glu Asn Tyr Ile Phe Gly Gln Cys Tyr
                245                 250                 255

Tyr Lys Ala Ser Asp Gly Ala Leu Phe Pro Leu Glu Val Thr Val Met
            260                 265                 270

Leu Asn Lys Arg Leu Pro Asp Ser Arg Thr Ser Tyr Val Met Thr Phe
        275                 280                 285

Leu Trp Ser Leu Asn Ala Gly Leu Ala Pro Glu Thr Thr Gln Ala Thr
290                 295                 300

Leu Ile Thr Ser Pro Phe Thr Phe Ser Tyr Ile Arg Glu Asp Asp
305                 310                 315

<210> SEQ ID NO 5
<211> LENGTH: 179
<212> TYPE: PRT
<213> ORGANISM: Human adenovirus serotype 12

<400> SEQUENCE: 5

Thr Leu Trp Thr Thr Pro Asp Pro Pro Asn Cys Ser Leu Ile Gln
1                 5                 10                  15

Glu Leu Asp Ala Lys Leu Thr Leu Cys Leu Thr Lys Asn Gly Ser Ile
            20                  25                  30

Val Asn Gly Ile Val Ser Leu Val Gly Val Lys Gly Asn Leu Leu Asn
        35                  40                  45

Ile Gln Ser Thr Thr Thr Val Gly Val His Leu Val Phe Asp Glu
    50                  55                  60

Gln Gly Arg Leu Ile Thr Ser Thr Pro Thr Ala Leu Val Pro Gln Ala
65                  70                  75                  80

Ser Trp Gly Tyr Arg Gln Gly Gln Ser Val Ser Thr Asn Thr Val Thr
                85                  90                  95

Asn Gly Leu Gly Phe Met Pro Asn Val Ser Ala Tyr Pro Arg Pro Asn
            100                 105                 110

Ala Ser Glu Ala Lys Ser Gln Met Val Ser Leu Thr Tyr Leu Gln Gly
        115                 120                 125

Asp Thr Ser Lys Pro Ile Thr Met Lys Val Ala Phe Asn Gly Ile Thr
130                 135                 140

Ser Leu Asn Gly Tyr Ser Leu Thr Phe Met Trp Ser Gly Leu Ser Asn
```

-continued

```
                145                 150                 155                 160
Tyr Ile Asn Gln Pro Phe Ser Thr Pro Ser Cys Ser Phe Ser Tyr Ile
                165                 170                 175
Thr Gln Glu

<210> SEQ ID NO 6
<211> LENGTH: 179
<212> TYPE: PRT
<213> ORGANISM: Human adenovirus serotype 31

<400> SEQUENCE: 6

Thr Leu Trp Thr Thr Pro Asp Pro Pro Asn Cys Thr Leu Arg Gln
1               5                   10                  15
Glu Leu Asp Ala Lys Leu Thr Leu Cys Leu Thr Lys Asn Glu Ser Ile
                20                  25                  30
Val Asn Gly Ile Val Ser Leu Ile Gly Val Lys Gly Asp Leu Leu His
                35                  40                  45
Ile Gln Pro Thr Thr Thr Thr Val Gly Leu His Leu Val Phe Asp Arg
            50                  55                  60
Gln Gly Arg Leu Val Thr Thr Thr Pro Thr Ala Leu Val Pro Gln Ala
65                  70                  75                  80
Ser Trp Gly Tyr Lys Gln Gly Gln Ser Val Ser Ser Ala Val Ala
                85                  90                  95
Asn Ala Leu Gly Phe Met Pro Asn Val Ser Ala Tyr Pro Arg Pro Asn
                100                 105                 110
Ala Gly Glu Ala Lys Ser Gln Met Leu Ser Gln Thr Tyr Leu Gln Gly
                115                 120                 125
Asp Thr Thr Lys Pro Ile Thr Met Lys Val Val Phe Asn Gly Asn Ala
                130                 135                 140
Thr Val Asp Gly Tyr Ser Leu Thr Phe Met Trp Thr Gly Val Ser Asn
145                 150                 155                 160
Tyr Leu Asn Gln Gln Phe Ser Thr Pro Ser Cys Ser Phe Ser Tyr Ile
                165                 170                 175
Ala Gln Glu

<210> SEQ ID NO 7
<211> LENGTH: 183
<212> TYPE: PRT
<213> ORGANISM: Human adenovirus serotype 2

<400> SEQUENCE: 7

Thr Leu Trp Thr Thr Pro Asp Pro Ser Pro Asn Cys Arg Ile His Ser
1               5                   10                  15
Asp Asn Asp Cys Lys Phe Thr Leu Val Leu Thr Lys Cys Gly Ser Gln
                20                  25                  30
Val Leu Ala Thr Val Ala Ala Leu Ala Val Ser Gly Asp Leu Ser Ser
                35                  40                  45
Met Thr Gly Thr Val Ala Ser Val Ser Ile Phe Leu Arg Phe Asp Gln
            50                  55                  60
Asn Gly Val Leu Met Glu Asn Ser Ser Leu Lys Lys His Tyr Trp Asn
65                  70                  75                  80
Phe Arg Asn Gly Asn Ser Thr Asn Ala Asn Pro Tyr Thr Asn Ala Val
                85                  90                  95
Gly Phe Met Pro Asn Leu Leu Ala Tyr Pro Lys Thr Gln Ser Gln Thr
                100                 105                 110
```

```
Ala Lys Asn Asn Ile Val Ser Gln Val Tyr Leu His Gly Asp Lys Thr
        115                 120                 125

Lys Pro Met Ile Leu Thr Ile Thr Leu Asn Gly Thr Ser Glu Ser Thr
    130                 135                 140

Glu Thr Ser Glu Val Ser Thr Tyr Ser Met Ser Phe Thr Trp Ser Trp
145                 150                 155                 160

Glu Ser Gly Lys Tyr Thr Thr Glu Thr Phe Ala Thr Asn Ser Tyr Thr
                165                 170                 175

Phe Ser Tyr Ile Ala Gln Glu
            180

<210> SEQ ID NO 8
<211> LENGTH: 182
<212> TYPE: PRT
<213> ORGANISM: Human adenovirus serotype 5

<400> SEQUENCE: 8

Thr Leu Trp Thr Thr Pro Ala Pro Ser Pro Asn Cys Arg Leu Asn Ala
1               5                   10                  15

Glu Lys Asp Ala Lys Leu Thr Leu Val Leu Thr Lys Cys Gly Ser Gln
            20                  25                  30

Ile Leu Ala Thr Val Ser Val Leu Ala Val Lys Gly Ser Leu Ala Pro
        35                  40                  45

Ile Ser Gly Thr Val Gln Ser Ala His Leu Ile Ile Arg Phe Asp Glu
    50                  55                  60

Asn Gly Val Leu Leu Asn Asn Ser Phe Leu Asp Pro Glu Tyr Trp Asn
65                  70                  75                  80

Phe Arg Asn Gly Asp Leu Thr Glu Gly Thr Ala Tyr Thr Asn Ala Val
                85                  90                  95

Gly Phe Met Pro Asn Leu Ser Ala Tyr Pro Lys Ser His Gly Lys Thr
            100                 105                 110

Ala Lys Ser Asn Ile Val Ser Gln Val Tyr Leu Asn Gly Asp Lys Thr
        115                 120                 125

Lys Pro Val Thr Leu Thr Ile Thr Leu Asn Gly Thr Gln Glu Thr Gly
    130                 135                 140

Asp Thr Thr Pro Ser Ala Tyr Ser Met Ser Phe Ser Trp Asp Trp Ser
145                 150                 155                 160

Gly His Asn Tyr Ile Asn Glu Ile Phe Ala Thr Ser Ser Tyr Thr Phe
                165                 170                 175

Ser Tyr Ile Ala Gln Glu
            180

<210> SEQ ID NO 9
<211> LENGTH: 182
<212> TYPE: PRT
<213> ORGANISM: Human adenovirus serotype 8

<400> SEQUENCE: 9

Thr Leu Trp Thr Thr Pro Asp Thr Ser Pro Asn Cys Arg Ile Asp Gln
1               5                   10                  15

Asp Lys Asp Ser Lys Leu Ser Leu Val Leu Thr Lys Cys Gly Ser Gln
            20                  25                  30

Ile Leu Ala Asn Val Ser Leu Ile Val Val Ala Gly Arg Tyr Lys Ile
        35                  40                  45

Ile Asn Asn Asn Thr Asn Pro Ala Leu Lys Gly Phe Thr Ile Lys Leu
    50                  55                  60
```

```
Leu Phe Asp Lys Asn Gly Val Leu Met Glu Ser Ser Asn Leu Gly Lys
 65                  70                  75                  80

Ser Tyr Trp Asn Phe Arg Asn Gln Asn Ser Ile Met Ser Thr Ala Tyr
                 85                  90                  95

Glu Lys Ala Ile Gly Phe Met Pro Asn Leu Val Ala Tyr Pro Lys Pro
            100                 105                 110

Thr Thr Gly Ser Lys Lys Tyr Ala Arg Asp Ile Val Tyr Gly Asn Ile
        115                 120                 125

Tyr Leu Gly Gly Lys Pro His Gln Pro Val Thr Ile Lys Thr Thr Phe
    130                 135                 140

Asn Gln Glu Thr Gly Cys Glu Tyr Ser Ile Thr Phe Asp Phe Ser Trp
145                 150                 155                 160

Ala Lys Thr Tyr Val Asn Val Glu Phe Glu Thr Thr Ser Phe Thr Phe
                165                 170                 175

Ser Tyr Ile Ala Gln Glu
            180
```

<210> SEQ ID NO 10
<211> LENGTH: 182
<212> TYPE: PRT
<213> ORGANISM: Human adenovirus serotype 9

<400> SEQUENCE: 10

```
Thr Leu Trp Thr Thr Pro Asp Thr Ser Pro Asn Cys Lys Ile Asp Gln
1               5                   10                  15

Asp Lys Asp Ser Lys Leu Thr Leu Val Leu Thr Lys Cys Gly Ser Gln
                20                  25                  30

Ile Leu Ala Asn Val Ser Leu Ile Val Val Asp Gly Lys Tyr Lys Ile
            35                  40                  45

Ile Asn Asn Asn Thr Gln Pro Ala Leu Lys Gly Phe Thr Ile Lys Leu
        50                  55                  60

Leu Phe Asp Glu Asn Gly Val Leu Met Glu Ser Ser Asn Leu Gly Lys
 65                  70                  75                  80

Ser Tyr Trp Asn Phe Arg Asn Glu Asn Ser Ile Met Ser Thr Ala Tyr
                 85                  90                  95

Glu Lys Ala Ile Gly Phe Met Pro Asn Leu Val Ala Tyr Pro Lys Pro
            100                 105                 110

Thr Ala Gly Ser Lys Lys Tyr Ala Arg Asp Ile Val Tyr Gly Asn Ile
        115                 120                 125

Tyr Leu Gly Gly Lys Pro Asp Gln Pro Val Thr Ile Lys Thr Thr Phe
    130                 135                 140

Asn Gln Glu Thr Gly Cys Glu Tyr Ser Ile Thr Phe Asp Phe Ser Trp
145                 150                 155                 160

Ala Lys Thr Tyr Val Asn Val Glu Phe Glu Thr Thr Ser Phe Thr Phe
                165                 170                 175

Ser Tyr Ile Ala Gln Glu
            180
```

<210> SEQ ID NO 11
<211> LENGTH: 187
<212> TYPE: PRT
<213> ORGANISM: Human adenovirus serotype 15

<400> SEQUENCE: 11

```
Thr Leu Trp Thr Thr Pro Asp Pro Ser Pro Asn Cys Lys Ile Ile Glu
1               5                   10                  15
```

-continued

```
Asp Lys Asp Ser Lys Leu Thr Leu Ile Leu Thr Lys Cys Gly Ser Gln
             20                  25                  30

Ile Leu Gly Ser Val Ser Leu Leu Val Val Lys Gly Lys Phe Ser Asn
         35                  40                  45

Ile Asn Asn Thr Thr Asn Pro Asn Glu Ala Asp Lys Gln Ile Thr Val
 50                  55                  60

Lys Leu Leu Phe Asp Ala Asn Gly Val Leu Lys Gln Gly Ser Thr Met
 65                  70                  75                  80

Asp Ser Ser Tyr Trp Asn Tyr Arg Ser Asp Asn Ser Asn Leu Ser Gln
                 85                  90                  95

Pro Tyr Lys Lys Ala Val Gly Phe Met Pro Ser Lys Thr Ala Tyr Pro
            100                 105                 110

Lys Gln Thr Lys Pro Thr Asn Lys Glu Ile Ser Gln Ala Lys Asn Lys
        115                 120                 125

Ile Val Ser Asn Val Tyr Leu Gly Gly Lys Ile Asp Gln Pro Cys Val
130                 135                 140

Ile Ile Ile Ser Phe Asn Glu Glu Ala Asp Ser Asp Tyr Ser Ile Val
145                 150                 155                 160

Phe Tyr Phe Lys Trp Tyr Lys Thr Tyr Glu Asn Val Gln Phe Asp Ser
                165                 170                 175

Ser Ser Phe Asn Phe Ser Tyr Ile Ala Gln Glu
            180                 185

<210> SEQ ID NO 12
<211> LENGTH: 182
<212> TYPE: PRT
<213> ORGANISM: Human adenovirus serotype 17

<400> SEQUENCE: 12

Thr Leu Trp Thr Thr Pro Asp Thr Ser Pro Asn Cys Arg Ile Asp Lys
1               5                  10                  15

Glu Lys Asp Ser Lys Leu Thr Leu Val Leu Thr Lys Cys Gly Ser Gln
             20                  25                  30

Ile Leu Ala Asn Val Ser Leu Ile Val Val Ser Gly Lys Tyr Gln Tyr
         35                  40                  45

Ile Asp His Ala Thr Asn Pro Thr Leu Lys Ser Phe Lys Ile Lys Leu
 50                  55                  60

Leu Phe Asp Asn Lys Gly Val Leu Leu Pro Ser Ser Asn Leu Asp Ser
65                  70                  75                  80

Thr Tyr Trp Asn Phe Arg Ser Asp Asn Leu Thr Val Ser Glu Ala Tyr
                 85                  90                  95

Lys Asn Ala Val Glu Phe Met Pro Asn Leu Val Ala Tyr Pro Lys Pro
            100                 105                 110

Thr Thr Gly Ser Lys Lys Tyr Ala Arg Asp Ile Val Tyr Gly Asn Ile
        115                 120                 125

Tyr Leu Gly Gly Leu Ala Tyr Gln Pro Val Val Ile Lys Val Thr Phe
130                 135                 140

Asn Glu Glu Ala Asp Ser Ala Tyr Ser Ile Thr Phe Glu Phe Val Trp
145                 150                 155                 160

Asn Lys Glu Tyr Ala Arg Val Glu Phe Glu Thr Thr Ser Phe Thr Phe
                165                 170                 175

Ser Tyr Ile Ala Gln Gln
            180

<210> SEQ ID NO 13
```

```
<211> LENGTH: 181
<212> TYPE: PRT
<213> ORGANISM: Human adenovirus serotype 19

<400> SEQUENCE: 13

Thr Leu Trp Thr Thr Pro Asp Thr Ser Pro Asn Cys Thr Ile Ala Gln
1               5                   10                  15

Asp Lys Asp Ser Lys Leu Thr Leu Val Leu Thr Lys Cys Gly Ser Gln
            20                  25                  30

Ile Leu Ala Asn Val Ser Leu Ile Val Ala Glu Arg Tyr His Ile
        35                  40                  45

Ile Asn Asn Lys Thr Asn Pro Glu Ile Lys Ser Phe Thr Ile Lys Leu
    50                  55                  60

Leu Phe Asn Lys Asn Gly Val Leu Leu Asp Asn Ser Asn Leu Gly Lys
65                  70                  75                  80

Ala Tyr Trp Asn Phe Arg Ser Gly Asn Ser Asn Val Ser Thr Ala Tyr
                85                  90                  95

Glu Lys Ala Ile Gly Phe Met Pro Asn Leu Val Ala Tyr Pro Lys Pro
            100                 105                 110

Ser Asn Ser Lys Lys Tyr Ala Arg Asp Ile Val Tyr Gly Thr Ile Tyr
        115                 120                 125

Leu Gly Gly Lys Pro Asp Gln Pro Ala Val Ile Lys Thr Thr Phe Asn
    130                 135                 140

Gln Glu Thr Gly Cys Glu Tyr Ser Ile Thr Phe Asp Phe Ser Trp Ser
145                 150                 155                 160

Lys Thr Tyr Glu Asn Val Glu Phe Glu Thr Thr Ser Phe Thr Phe Ser
                165                 170                 175

Tyr Ile Ala Gln Glu
            180

<210> SEQ ID NO 14
<211> LENGTH: 179
<212> TYPE: PRT
<213> ORGANISM: Human adenovirus serotype 28

<400> SEQUENCE: 14

Thr Leu Trp Thr Thr Pro Asp Thr Ser Pro Asn Cys Lys Met Ser Glu
1               5                   10                  15

Val Lys Asp Ser Lys Leu Thr Leu Ile Leu Thr Lys Cys Gly Ser Gln
            20                  25                  30

Ile Leu Gly Ser Val Ser Leu Leu Ala Val Lys Gly Glu Tyr Gln Asn
        35                  40                  45

Met Thr Ala Ser Thr Asn Lys Asn Val Lys Ile Thr Leu Leu Phe Asp
    50                  55                  60

Ala Asn Gly Val Leu Leu Glu Gly Ser Ser Leu Asp Lys Glu Tyr Trp
65                  70                  75                  80

Asn Phe Arg Asn Asn Asp Ser Thr Val Ser Gly Lys Tyr Glu Asn Ala
                85                  90                  95

Val Pro Phe Met Pro Asn Ile Thr Ala Tyr Lys Pro Val Asn Ser Lys
            100                 105                 110

Ser Tyr Ala Arg Ser His Ile Phe Gly Asn Val Tyr Ile Asp Ala Lys
        115                 120                 125

Pro Tyr Asn Pro Val Val Ile Lys Ile Ser Phe Asn Gln Glu Thr Gln
    130                 135                 140

Asn Asn Cys Val Tyr Ser Ile Ser Phe Asp Tyr Thr Cys Ser Lys Glu
145                 150                 155                 160
```

-continued

Tyr Thr Gly Met Gln Phe Asp Val Thr Ser Phe Thr Phe Ser Tyr Ile
                165                 170                 175

Ala Gln Glu

<210> SEQ ID NO 15
<211> LENGTH: 181
<212> TYPE: PRT
<213> ORGANISM: Human adenovirus serotype 37

<400> SEQUENCE: 15

Thr Leu Trp Thr Thr Pro Asp Thr Ser Pro Asn Cys Thr Ile Ala Gln
1               5                   10                  15

Asp Lys Asp Ser Lys Leu Thr Leu Val Leu Thr Lys Cys Gly Ser Gln
            20                  25                  30

Ile Leu Ala Asn Val Ser Leu Ile Val Val Ala Gly Lys Tyr His Ile
        35                  40                  45

Ile Asn Asn Lys Thr Asn Pro Lys Ile Lys Ser Phe Thr Ile Lys Leu
    50                  55                  60

Leu Phe Asn Lys Asn Gly Val Leu Leu Asp Asn Ser Asn Leu Gly Lys
65                  70                  75                  80

Ala Tyr Trp Asn Phe Arg Ser Gly Asn Ser Asn Val Ser Thr Ala Tyr
                85                  90                  95

Glu Lys Ala Ile Gly Phe Met Pro Asn Leu Val Ala Val Ser Lys Pro
            100                 105                 110

Ser Asn Ser Lys Lys Tyr Ala Arg Asp Ile Val Tyr Gly Asn Ile Tyr
        115                 120                 125

Leu Gly Gly Lys Pro Asp Gln Pro Gly Val Ile Lys Thr Thr Phe Asn
    130                 135                 140

Gln Glu Thr Gly Cys Glu Tyr Ser Ile Thr Phe Asn Phe Ser Trp Ser
145                 150                 155                 160

Lys Thr Tyr Glu Asn Val Glu Phe Glu Thr Thr Ser Phe Thr Phe Ser
                165                 170                 175

Tyr Ile Ala Gln Glu
            180

<210> SEQ ID NO 16
<211> LENGTH: 179
<212> TYPE: PRT
<213> ORGANISM: Human adenovirus serotype 4

<400> SEQUENCE: 16

Thr Leu Trp Thr Thr Pro Asp Pro Ser Pro Asn Cys Gln Ile Leu Ala
1               5                   10                  15

Glu Asn Asp Ala Lys Leu Thr Leu Cys Leu Thr Met Cys Asp Ser Gln
            20                  25                  30

Ile Leu Ala Thr Val Ser Val Leu Val Val Arg Ser Gly Asn Leu Asn
        35                  40                  45

Pro Ile Thr Gly Thr Val Ser Ser Ala Gln Val Phe Leu Arg Phe Asp
    50                  55                  60

Ala Asn Gly Val Leu Leu Thr Glu His Ser Ser Lys Lys Tyr Trp
65                  70                  75                  80

Gly Tyr Lys Gln Gly Asp Ser Ile Asp Gly Thr Pro Tyr Thr Asn Ala
                85                  90                  95

Val Gly Phe Met Pro Asn Ser Thr Ala Tyr Pro Lys Thr Gln Ser Ser
            100                 105                 110

-continued

Thr Thr Lys Asn Asn Ile Val Gly Gln Val Tyr Met Asn Gly Asp Val
            115                 120                 125

Ser Lys Pro Met Leu Leu Thr Ile Thr Leu Asn Gly Thr Asp Asp Thr
        130                 135                 140

Thr Ser Ala Tyr Ser Met Ser Phe Ser Tyr Thr Trp Thr Asn Gly Ser
145                 150                 155                 160

Tyr Ile Gly Ala Thr Phe Gly Ala Asn Ser Tyr Thr Phe Ser Tyr Ile
                165                 170                 175

Ala Gln Gln

<210> SEQ ID NO 17
<211> LENGTH: 176
<212> TYPE: PRT
<213> ORGANISM: Human adenovirus serotype 40LONG

<400> SEQUENCE: 17

Thr Leu Trp Thr Thr Ala Asp Pro Ser Pro Asn Ala Thr Phe Tyr Glu
1               5                   10                  15

Ser Leu Asp Ala Lys Val Trp Leu Val Leu Val Lys Cys Asn Gly Met
            20                  25                  30

Val Asn Gly Thr Ile Ser Ile Lys Ala Gln Lys Gly Thr Leu Leu Lys
        35                  40                  45

Pro Thr Ala Ser Phe Ile Ser Phe Val Met Tyr Phe Tyr Ser Asp Gly
    50                  55                  60

Thr Trp Arg Lys Asn Tyr Pro Val Phe Asp Asn Glu Gly Ile Leu Ala
65                  70                  75                  80

Asn Ser Ala Thr Trp Gly Tyr Arg Gln Gly Gln Ser Ala Asn Thr Asn
                85                  90                  95

Val Ser Asn Ala Val Glu Phe Met Pro Ser Ser Lys Arg Tyr Pro Asn
            100                 105                 110

Glu Lys Gly Ser Glu Val Gln Asn Met Ala Leu Thr Tyr Thr Phe Leu
        115                 120                 125

Gln Gly Asp Pro Asn Met Ala Ile Ser Phe Gln Ser Ile Tyr Asn His
    130                 135                 140

Ala Ile Glu Gly Tyr Ser Leu Lys Phe Thr Trp Arg Val Arg Asn Asn
145                 150                 155                 160

Glu Arg Phe Asp Ile Pro Cys Cys Ser Phe Ser Tyr Val Thr Glu Gln
                165                 170                 175

<210> SEQ ID NO 18
<211> LENGTH: 176
<212> TYPE: PRT
<213> ORGANISM: Human adenovirus serotype 41LONG

<400> SEQUENCE: 18

Thr Leu Trp Thr Thr Ala Asp Pro Ser Pro Asn Ala Thr Phe Tyr Glu
1               5                   10                  15

Ser Leu Asp Ala Lys Val Trp Leu Val Leu Val Lys Cys Asn Gly Met
            20                  25                  30

Val Asn Gly Thr Ile Ser Ile Lys Ala Gln Lys Gly Ile Leu Leu Arg
        35                  40                  45

Pro Thr Ala Ser Phe Ile Ser Phe Val Met Tyr Phe Tyr Ser Asp Gly
    50                  55                  60

Thr Trp Arg Lys Asn Tyr Pro Val Phe Asp Asn Glu Gly Ile Leu Ala
65                  70                  75                  80

Asn Ser Ala Thr Trp Gly Tyr Arg Gln Gly Gln Ser Ala Asn Thr Asn

```
                         85                  90                  95
Val Ser Asn Ala Val Glu Phe Met Pro Ser Ser Lys Arg Tyr Pro Asn
                100                 105                 110

Gln Lys Gly Ser Glu Val Gln Asn Met Ala Leu Thr Tyr Thr Phe Leu
            115                 120                 125

Gln Gly Asp Pro Asn Met Ala Ile Ser Phe Gln Ser Ile Tyr Asn His
        130                 135                 140

Ala Leu Glu Gly Tyr Ser Leu Lys Phe Thr Trp Arg Val Arg Asn Asn
145                 150                 155                 160

Glu Arg Phe Asp Ile Pro Cys Cys Ser Phe Ser Tyr Val Thr Glu Gln
                165                 170                 175

<210> SEQ ID NO 19
<211> LENGTH: 188
<212> TYPE: PRT
<213> ORGANISM: Human adenovirus serotype 3

<400> SEQUENCE: 19

Thr Leu Trp Thr Gly Pro Lys Pro Glu Ala Asn Cys Ile Ile Glu Tyr
1               5                   10                  15

Gly Lys Gln Asn Pro Asp Ser Lys Leu Thr Leu Ile Leu Val Lys Asn
            20                  25                  30

Gly Gly Ile Val Asn Gly Tyr Val Thr Leu Met Gly Ala Ser Asp Tyr
        35                  40                  45

Val Asn Thr Leu Phe Lys Asn Lys Asn Val Ser Ile Asn Val Glu Leu
    50                  55                  60

Tyr Phe Asp Ala Thr Gly His Ile Leu Pro Asp Ser Ser Ser Leu Lys
65                  70                  75                  80

Thr Asp Leu Glu Leu Lys Tyr Lys Gln Thr Ala Asp Phe Ser Ala Arg
                85                  90                  95

Gly Phe Met Pro Ser Thr Thr Ala Tyr Pro Phe Val Leu Pro Asn Ala
                100                 105                 110

Gly Thr His Asn Glu Asn Tyr Ile Phe Gly Gln Cys Tyr Tyr Lys Ala
            115                 120                 125

Ser Asp Gly Ala Leu Phe Pro Leu Glu Val Thr Val Met Leu Asn Lys
        130                 135                 140

Arg Leu Pro Asp Ser Arg Thr Ser Tyr Val Met Thr Phe Leu Trp Ser
145                 150                 155                 160

Leu Asn Ala Gly Leu Ala Pro Glu Thr Thr Gln Ala Thr Leu Ile Thr
                165                 170                 175

Ser Pro Phe Thr Phe Ser Tyr Ile Arg Glu Asp Asp
            180                 185

<210> SEQ ID NO 20
<211> LENGTH: 193
<212> TYPE: PRT
<213> ORGANISM: Human adenovirus serotype 7

<400> SEQUENCE: 20

Thr Leu Trp Thr Gly Val Asn Pro Thr Thr Ala Asn Cys Gln Ile Met
1               5                   10                  15

Ala Ser Ser Glu Ser Asn Asp Cys Lys Leu Ile Leu Thr Leu Val Lys
            20                  25                  30

Thr Gly Gly Leu Val Thr Ala Phe Val Tyr Val Ile Gly Val Ser Asn
        35                  40                  45

Asp Phe Asn Met Leu Thr Thr His Lys Asn Ile Asn Phe Thr Ala Glu
```

-continued

```
                50                  55                  60
Leu Phe Phe Asp Ser Thr Gly Asn Leu Leu Thr Ser Leu Ser Ser Leu
 65                  70                  75                  80

Lys Thr Pro Leu Asn His Lys Ser Gly Gln Asn Met Ala Thr Gly Ala
                 85                  90                  95

Leu Thr Asn Ala Lys Gly Phe Met Pro Ser Thr Thr Ala Tyr Pro Phe
                100                 105                 110

Asn Val Asn Ser Arg Glu Lys Glu Asn Tyr Ile Tyr Gly Thr Cys Tyr
                115                 120                 125

Tyr Thr Ala Ser Asp His Thr Ala Phe Pro Ile Asp Ile Ser Val Met
                130                 135                 140

Leu Asn Gln Arg Ala Leu Asn Asn Glu Thr Ser Tyr Cys Ile Arg Val
145                 150                 155                 160

Thr Trp Ser Trp Asn Thr Gly Val Ala Pro Glu Val Gln Thr Ser Ala
                165                 170                 175

Thr Thr Leu Val Thr Ser Pro Phe Thr Phe Tyr Tyr Ile Arg Glu Asp
                180                 185                 190

Asp
```

<210> SEQ ID NO 21
<211> LENGTH: 193
<212> TYPE: PRT
<213> ORGANISM: Human adenovirus serotype 11A

<400> SEQUENCE: 21

```
Thr Leu Trp Thr Gly Ile Asn Pro Thr Glu Ala Asn Cys Gln Met Met
 1               5                  10                  15

Asp Ser Ser Glu Ser Asn Asp Cys Lys Leu Ile Leu Thr Leu Val Lys
                 20                  25                  30

Thr Gly Ala Leu Val Thr Ala Phe Val Tyr Val Ile Gly Val Ser Asn
                 35                  40                  45

Asn Phe Asn Met Leu Thr Thr Tyr Arg Asn Ile Asn Phe Thr Ala Glu
                 50                  55                  60

Leu Phe Phe Asp Ser Ala Gly Asn Leu Leu Thr Ser Leu Ser Ser Leu
 65                  70                  75                  80

Lys Thr Pro Leu Asn His Lys Ser Gly Gln Asn Met Ala Thr Gly Ala
                 85                  90                  95

Ile Thr Asn Ala Lys Ser Phe Met Pro Ser Thr Thr Ala Tyr Pro Phe
                100                 105                 110

Asn Asn Asn Ser Arg Glu Lys Glu Asn Tyr Ile Tyr Gly Thr Cys His
                115                 120                 125

Tyr Thr Ala Ser Asp His Thr Ala Phe Pro Ile Asp Ile Ser Val Met
                130                 135                 140

Leu Asn Gln Arg Ala Ile Arg Ala Asp Thr Ser Tyr Cys Ile Arg Ile
145                 150                 155                 160

Thr Trp Ser Trp Asn Thr Gly Asp Ala Pro Glu Gly Gln Thr Ser Ala
                165                 170                 175

Thr Thr Leu Val Thr Ser Pro Phe Thr Phe Tyr Tyr Ile Arg Glu Asp
                180                 185                 190

Asp
```

<210> SEQ ID NO 22
<211> LENGTH: 192
<212> TYPE: PRT
<213> ORGANISM: Human adenovirus serotype 16

```
<400> SEQUENCE: 22

Thr Leu Trp Thr Gly Ala Lys Pro Ser Ala Asn Cys Val Ile Lys Glu
1               5                   10                  15

Gly Glu Asp Ser Pro Asp Cys Lys Leu Thr Leu Val Leu Val Lys Asn
            20                  25                  30

Gly Gly Leu Ile Asn Gly Tyr Ile Thr Leu Met Gly Ala Ser Glu Tyr
        35                  40                  45

Thr Asn Thr Leu Phe Lys Asn Asn Gln Val Thr Ile Asp Val Asn Leu
    50                  55                  60

Ala Phe Asp Asn Thr Gly Gln Ile Ile Thr Tyr Leu Ser Ser Leu Lys
65                  70                  75                  80

Ser Asn Leu Asn Phe Lys Asp Asn Gln Asn Met Ala Thr Gly Thr Ile
                85                  90                  95

Thr Ser Ala Lys Gly Phe Met Pro Ser Thr Thr Ala Tyr Pro Phe Ile
            100                 105                 110

Thr Tyr Ala Thr Glu Thr Leu Asn Glu Asp Tyr Ile Tyr Gly Glu Cys
        115                 120                 125

Tyr Tyr Lys Ser Thr Asn Gly Thr Leu Phe Pro Leu Lys Val Thr Val
130                 135                 140

Thr Leu Asn Arg Arg Met Leu Ala Ser Gly Met Ala Tyr Ala Met Asn
145                 150                 155                 160

Phe Ser Trp Ser Leu Asn Ala Glu Glu Ala Pro Glu Thr Thr Glu Val
                165                 170                 175

Thr Leu Ile Thr Ser Pro Phe Phe Phe Ser Tyr Ile Arg Glu Asp Asp
            180                 185                 190

<210> SEQ ID NO 23
<211> LENGTH: 191
<212> TYPE: PRT
<213> ORGANISM: Human adenovirus serotype 21

<400> SEQUENCE: 23

Thr Leu Trp Thr Gly Ile Lys Pro Pro Asn Cys Gln Ile Val Glu
1               5                   10                  15

Asn Thr Asp Thr Asn Asp Gly Lys Leu Thr Leu Val Leu Val Lys Asn
            20                  25                  30

Gly Gly Leu Val Asn Gly Tyr Val Ser Leu Val Gly Val Ser Asp Thr
        35                  40                  45

Val Asn Gln Met Phe Thr Gln Lys Ser Ala Thr Ile Gln Leu Arg Leu
    50                  55                  60

Tyr Phe Asp Ser Ser Gly Asn Leu Leu Thr Asp Glu Ser Asn Leu Lys
65                  70                  75                  80

Ile Pro Leu Lys Asn Lys Ser Ser Thr Ala Thr Ser Glu Val Leu Gln
                85                  90                  95

Pro Ala Glu Ala Phe Met Pro Ser Thr Thr Ala Tyr Pro Phe Asn Thr
            100                 105                 110

Thr Thr Arg Asp Ser Glu Asn Tyr Ile His Gly Ile Cys Tyr Tyr Met
        115                 120                 125

Thr Ser Tyr Asp Arg Ser Leu Val Pro Leu Asn Ile Ser Ile Met Leu
130                 135                 140

Asn Ser Arg Thr Ile Ser Ser Asn Val Ala Tyr Ala Ile Gln Phe Glu
145                 150                 155                 160

Trp Asn Leu Asn Ala Lys Glu Ser Pro Glu Ser Asn Ile Ala Thr Leu
                165                 170                 175
```

-continued

```
Thr Thr Ser Pro Phe Phe Phe Ser Tyr Ile Arg Glu Asp Asn
        180                 185                 190
```

<210> SEQ ID NO 24
<211> LENGTH: 193
<212> TYPE: PRT
<213> ORGANISM: Human adenovirus serotype 34A

<400> SEQUENCE: 24

```
Thr Leu Trp Thr Gly Val Asn Pro Thr Glu Ala Asn Cys Gln Ile Met
1               5                   10                  15
Asn Ser Ser Glu Ser Asn Asp Cys Lys Leu Ile Leu Thr Leu Val Lys
            20                  25                  30
Thr Gly Ala Leu Val Thr Ala Phe Val Tyr Val Ile Gly Val Ser Asn
        35                  40                  45
Asn Phe Asn Met Leu Thr Thr His Arg Asn Ile Asn Phe Thr Ala Glu
    50                  55                  60
Leu Phe Phe Asp Ser Thr Gly Asn Leu Leu Thr Arg Leu Ser Ser Leu
65                  70                  75                  80
Lys Thr Pro Leu Asn His Lys Ser Gly Gln Asn Met Ala Thr Gly Ala
                85                  90                  95
Ile Thr Asn Ala Lys Gly Phe Met Pro Ser Thr Thr Ala Tyr Pro Phe
            100                 105                 110
Asn Asp Asn Ser Arg Glu Lys Glu Asn Tyr Ile Tyr Gly Thr Cys Tyr
        115                 120                 125
Tyr Thr Ala Ser Asp His Thr Ala Phe Pro Ile Asp Ile Ser Val Met
    130                 135                 140
Leu Asn Arg Arg Ala Ile Asn Asp Glu Thr Ser Tyr Cys Ile Arg Ile
145                 150                 155                 160
Thr Trp Ser Trp Asn Thr Gly Asp Ala Pro Glu Val Gln Thr Ser Ala
                165                 170                 175
Thr Thr Leu Val Thr Ser Pro Phe Thr Phe Tyr Tyr Ile Arg Glu Asp
            180                 185                 190
Asp
```

<210> SEQ ID NO 25
<211> LENGTH: 191
<212> TYPE: PRT
<213> ORGANISM: Human adenovirus serotype 35

<400> SEQUENCE: 25

```
Thr Leu Trp Thr Gly Ile Asn Pro Pro Asn Cys Gln Ile Val Glu
1               5                   10                  15
Asn Thr Asn Thr Asn Asp Gly Lys Leu Thr Leu Val Leu Val Lys Asn
            20                  25                  30
Gly Gly Leu Val Asn Gly Tyr Val Ser Leu Val Gly Val Ser Asp Thr
        35                  40                  45
Val Asn Gln Met Phe Thr Gln Lys Thr Ala Asn Ile Gln Leu Arg Leu
    50                  55                  60
Tyr Phe Asp Ser Ser Gly Asn Leu Leu Thr Glu Glu Ser Asp Leu Lys
65                  70                  75                  80
Ile Pro Leu Lys Asn Lys Ser Ser Thr Ala Thr Ser Glu Thr Val Ala
                85                  90                  95
Ser Ser Lys Ala Phe Met Pro Ser Thr Thr Ala Tyr Pro Phe Asn Thr
            100                 105                 110
```

-continued

```
Thr Thr Arg Asp Ser Glu Asn Tyr Ile His Gly Ile Cys Tyr Tyr Met
        115                 120                 125

Thr Ser Tyr Asp Arg Ser Leu Phe Pro Leu Asn Ile Ser Ile Met Leu
130                 135                 140

Asn Ser Arg Met Ile Ser Ser Asn Val Ala Tyr Ala Ile Gln Phe Glu
145                 150                 155                 160

Trp Asn Leu Asn Ala Ser Glu Ser Pro Glu Ser Asn Ile Ala Thr Leu
                165                 170                 175

Thr Thr Ser Pro Phe Phe Phe Ser Tyr Ile Thr Glu Asp Asp Asn
                180                 185                 190

<210> SEQ ID NO 26
<211> LENGTH: 156
<212> TYPE: PRT
<213> ORGANISM: Human adenovirus serotype 40SHORT

<400> SEQUENCE: 26

Thr Ile Trp Ser Ile Ser Pro Thr Pro Asn Cys Ser Ile Tyr Glu Thr
1               5                   10                  15

Gln Asp Ala Asn Leu Phe Leu Cys Leu Thr Lys Asn Gly Ala His Val
                20                  25                  30

Leu Gly Thr Ile Thr Ile Lys Gly Leu Lys Gly Ala Leu Arg Glu Met
            35                  40                  45

Asn Asp Asn Ala Leu Ser Val Lys Leu Pro Phe Asp Asn Gln Gly Asn
50                  55                  60

Leu Leu Asn Cys Ala Leu Glu Ser Ser Thr Trp Arg Tyr Gln Glu Thr
65                  70                  75                  80

Asn Ala Val Ala Ser Asn Ala Leu Thr Phe Met Pro Asn Ser Thr Val
                85                  90                  95

Tyr Pro Arg Asn Lys Thr Ala Asp Pro Gly Asn Met Leu Ile Gln Ile
                100                 105                 110

Ser Pro Asn Ile Thr Phe Ser Val Val Tyr Asn Glu Ile Asn Ser Gly
            115                 120                 125

Tyr Ala Phe Thr Phe Lys Trp Ser Ala Glu Pro Gly Lys Pro Phe His
        130                 135                 140

Pro Pro Thr Ala Val Phe Cys Tyr Ile Thr Glu Gln
145                 150                 155

<210> SEQ ID NO 27
<211> LENGTH: 156
<212> TYPE: PRT
<213> ORGANISM: Human adenovirus serotype 41SHORT

<400> SEQUENCE: 27

Thr Ile Trp Ser Ile Ser Pro Thr Pro Asn Cys Ser Ile Tyr Glu Thr
1               5                   10                  15

Gln Asp Ala Asn Leu Phe Leu Cys Leu Thr Lys Asn Gly Ala His Val
                20                  25                  30

Leu Gly Thr Ile Thr Ile Lys Gly Leu Lys Gly Ala Leu Arg Glu Met
            35                  40                  45

His Asp Asn Ala Leu Ser Leu Lys Leu Pro Phe Asp Asn Gln Gly Asn
50                  55                  60

Leu Leu Asn Cys Ala Leu Glu Ser Ser Thr Trp Arg Tyr Gln Glu Thr
65                  70                  75                  80

Asn Ala Val Ala Ser Asn Ala Leu Thr Phe Met Pro Asn Ser Thr Val
                85                  90                  95
```

```
Tyr Pro Arg Asn Lys Thr Ala His Pro Gly Asn Met Leu Ile Gln Ile
            100                 105                 110

Ser Pro Asn Ile Thr Phe Ser Val Val Tyr Asn Glu Ile Asn Ser Gly
            115                 120                 125

Tyr Ala Phe Thr Phe Lys Trp Ser Ala Glu Pro Gly Lys Pro Phe His
            130                 135                 140

Pro Pro Thr Ala Val Phe Cys Tyr Ile Thr Glu Gln
145                 150                 155

<210> SEQ ID NO 28
<211> LENGTH: 354
<212> TYPE: PRT
<213> ORGANISM: Anti-HA ScFv fused in frame with 2 C-terminal myc
      epitopes and PDGF receptor transmembrane anchor
      (Anti-HA pseudo-receptor)

<400> SEQUENCE: 28

Met Glu Thr Asp Thr Leu Leu Leu Trp Val Leu Leu Leu Trp Val Pro
 1               5                  10                  15

Gly Ser Thr Gly Asp Gly Ala Gln Pro Ala Asp Ile Val Met Thr Gln
            20                  25                  30

Ser Pro Ser Ser Leu Thr Val Thr Ala Gly Glu Lys Val Thr Met Ser
            35                  40                  45

Cys Lys Ser Ser Gln Ser Leu Leu Asn Ser Gly Asn Gln Lys Asn Tyr
            50                  55                  60

Leu Thr Trp Tyr Gln Gln Lys Pro Gly Gln Pro Pro Lys Leu Leu Ile
 65                  70                  75                  80

Tyr Trp Ala Ser Thr Arg Glu Ser Gly Val Pro Asp Arg Phe Thr Gly
            85                  90                  95

Ser Gly Ser Gly Arg Asp Phe Thr Leu Thr Ile Ser Ser Val Gln Ala
            100                 105                 110

Glu Asp Leu Ala Val Tyr Tyr Cys Gln Asn Asp Asn Ser His Pro Leu
            115                 120                 125

Thr Phe Gly Ala Gly Thr Lys Leu Glu Leu Lys Arg Ala Gly Gly Gly
            130                 135                 140

Gly Ser Gly Gly Gly Gly Ser Gly Gly Gly Gly Ser Glu Val Gln Leu
145                 150                 155                 160

Val Glu Ser Gly Gly Asn Leu Val Asn Pro Gly Gly Ser Leu Lys Leu
            165                 170                 175

Ser Cys Ala Ala Ser Gly Phe Thr Phe Ser Thr Tyr Gly Met Ser Trp
            180                 185                 190

Val Arg Gln Thr Pro Asn Lys Arg Leu Glu Trp Val Pro Thr Ile Ile
            195                 200                 205

Arg Gly Gly Ser Tyr Thr Tyr Tyr Pro Asp Ser Val Lys Gly Arg Phe
            210                 215                 220

Thr Ile Ser Lys Asn Asn Ala Lys Asn Thr Leu Tyr Leu Gln Met Ser
225                 230                 235                 240

Ser Leu Lys Ser Glu Asp Thr Ala Met Tyr Tyr Cys Ala Lys Arg Glu
            245                 250                 255

Thr Phe Asp Glu Lys Gly Phe Ala Tyr Trp Gly Gln Gly Thr Leu Val
            260                 265                 270

Thr Val Ser Ala Ala Ala Ala Glu Gln Lys Leu Ile Ser Glu Glu Asp
            275                 280                 285

Leu Asn Gly Ala Val Asp Glu Gln Lys Leu Ile Ser Glu Glu Asp Leu
            290                 295                 300
```

```
Asn Ala Val Gly Gln Asp Thr Gln Glu Val Ile Val Pro His Ser
305                 310                 315                 320

Leu Pro Phe Lys Val Val Ile Ser Ala Ile Leu Ala Leu Val Val
                325                 330                 335

Leu Thr Ile Ile Ser Leu Ile Ile Leu Ile Met Leu Trp Gln Lys Lys
                340                 345                 350

Pro Val

<210> SEQ ID NO 29
<211> LENGTH: 218
<212> TYPE: PRT
<213> ORGANISM: Artificial Sequence
<220> FEATURE:
<223> OTHER INFORMATION: Description of Artificial Sequence: Consensus
      sequence from the comparison between non-group B
      adenoviral knobs.
<221> NAME/KEY: PEPTIDE
<222> LOCATION: (7)
<223> OTHER INFORMATION: Xaa is any amino acid or no amino acid
<221> NAME/KEY: PEPTIDE
<222> LOCATION: (13)..(17)
<223> OTHER INFORMATION: Xaa is any amino acid or no amino acid
<221> NAME/KEY: PEPTIDE
<222> LOCATION: (20)
<223> OTHER INFORMATION: Xaa is any amino acid or no amino acid
<221> NAME/KEY: PEPTIDE
<222> LOCATION: (36)
<223> OTHER INFORMATION: Xaa is any amino acid or no amino acid
<221> NAME/KEY: PEPTIDE
<222> LOCATION: (39)..(41)
<223> OTHER INFORMATION: Xaa is any amino acid or no amino acid
<221> NAME/KEY: PEPTIDE
<222> LOCATION: (43)..(46)
<223> OTHER INFORMATION: Xaa is any amino acid or no amino acid
<221> NAME/KEY: PEPTIDE
<222> LOCATION: (48)..(51)
<223> OTHER INFORMATION: Xaa is any amino acid or no amino acid
<221> NAME/KEY: PEPTIDE
<222> LOCATION: (52)..(84)
<223> OTHER INFORMATION: Xaa is any amino acid or no amino acid
<221> NAME/KEY: PEPTIDE
<222> LOCATION: (87)
<223> OTHER INFORMATION: Xaa is any amino acid or no amino acid
<221> NAME/KEY: PEPTIDE
<222> LOCATION: (92)..(94)
<223> OTHER INFORMATION: Xaa is any amino acid or no amino acid
<221> NAME/KEY: PEPTIDE
<222> LOCATION: (96)..(99)
<223> OTHER INFORMATION: Xaa is any amino acid or no amino acid
<221> NAME/KEY: PEPTIDE
<222> LOCATION: (101)..(103)
<223> OTHER INFORMATION: Xaa is any amino acid or no amino acid
<221> NAME/KEY: PEPTIDE
<222> LOCATION: (109)
<223> OTHER INFORMATION: Xaa is any amino acid or no amino acid
<221> NAME/KEY: PEPTIDE
<222> LOCATION: (111)..(117)
<223> OTHER INFORMATION: Xaa is any amino acid or no amino acid
<221> NAME/KEY: PEPTIDE
<222> LOCATION: (119)
<223> OTHER INFORMATION: Xaa is any amino acid or no amino acid
<221> NAME/KEY: PEPTIDE
<222> LOCATION: (128)..(129)
<223> OTHER INFORMATION: Xaa is any amino acid or no amino acid
<221> NAME/KEY: PEPTIDE
<222> LOCATION: (134)..(144)
<223> OTHER INFORMATION: Xaa is any amino acid or no amino acid
<221> NAME/KEY: PEPTIDE
<222> LOCATION: (146)..(149)
<223> OTHER INFORMATION: Xaa is any amino acid or no amino acid
<221> NAME/KEY: PEPTIDE
<222> LOCATION: (152)..(155)
<223> OTHER INFORMATION: Xaa is any amino acid or no amino acid
<221> NAME/KEY: PEPTIDE
<222> LOCATION: (160)..(163)
```

```
<223> OTHER INFORMATION: Xaa is any amino acid or no amino acid
<221> NAME/KEY: PEPTIDE
<222> LOCATION: (165)..(169)
<223> OTHER INFORMATION: Xaa is any amino acid or no amino acid
<221> NAME/KEY: PEPTIDE
<222> LOCATION: (171)
<223> OTHER INFORMATION: Xaa is any amino acid or no amino acid
<221> NAME/KEY: PEPTIDE
<222> LOCATION: (173)..(175)
<223> OTHER INFORMATION: Xaa is any amino acid or no amino acid
<221> NAME/KEY: PEPTIDE
<222> LOCATION: (178)..(185)
<223> OTHER INFORMATION: Xaa is any amino acid or no amino acid
<221> NAME/KEY: PEPTIDE
<222> LOCATION: (188)..(189)
<223> OTHER INFORMATION: Xaa is any amino acid or no amino acid
<221> NAME/KEY: PEPTIDE
<222> LOCATION: (191)..(193)
<223> OTHER INFORMATION: Xaa is any amino acid or no amino acid
<221> NAME/KEY: PEPTIDE
<222> LOCATION: (196)..(199)
<223> OTHER INFORMATION: Xaa is any amino acid or no amino acid
<221> NAME/KEY: PEPTIDE
<222> LOCATION: (201)
<223> OTHER INFORMATION: Xaa is any amino acid or no amino acid
<221> NAME/KEY: PEPTIDE
<222> LOCATION: (203)..(204)
<223> OTHER INFORMATION: Xaa is any amino acid or no amino acid
<221> NAME/KEY: PEPTIDE
<222> LOCATION: (206)
<223> OTHER INFORMATION: Xaa is any amino acid or no amino acid
<221> NAME/KEY: PEPTIDE
<222> LOCATION: (208)
<223> OTHER INFORMATION: Xaa is any amino acid or no amino acid
<221> NAME/KEY: PEPTIDE
<222> LOCATION: (210)
<223> OTHER INFORMATION: Xaa is any amino acid or no amino acid

<400> SEQUENCE: 29

Thr Leu Trp Thr Thr Pro Xaa Pro Ser Pro Asn Cys Xaa Xaa Xaa Xaa
 1               5                  10                  15

Xaa Lys Asp Xaa Lys Leu Thr Leu Val Leu Thr Lys Cys Gly Ser Gln
             20                  25                  30

Ile Leu Ala Xaa Val Ser Xaa Xaa Xaa Val Xaa Xaa Xaa Xaa Gly Xaa
         35                  40                  45

Xaa Xaa Xaa Ile Xaa Xaa Xaa Xaa Xaa Xaa Xaa Xaa Xaa Xaa Xaa Xaa
     50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Phe Asp Xaa Asn Gly Val Leu Xaa Xaa Xaa Ser Xaa
                 85                  90                  95

Xaa Xaa Xaa Leu Xaa Xaa Xaa Tyr Trp Asn Phe Arg Xaa Gly Xaa Xaa
            100                 105                 110

Xaa Xaa Xaa Xaa Xaa Tyr Xaa Asn Ala Val Gly Phe Met Pro Asn Xaa
            115                 120                 125

Xaa Ala Tyr Pro Lys Xaa Xaa Xaa Xaa Xaa Xaa Xaa Xaa Xaa Xaa Xaa
130                 135                 140

Ala Xaa Xaa Xaa Xaa Ile Val Xaa Xaa Xaa Tyr Leu Xaa Gly Xaa
145                 150                 155                 160

Xaa Xaa Xaa Pro Xaa Xaa Xaa Xaa Xaa Thr Xaa Asn Xaa Xaa Xaa Glu
            165                 170                 175

Xaa Xaa Xaa Xaa Xaa Xaa Xaa Xaa Tyr Ser Xaa Xaa Phe Xaa Xaa
            180                 185                 190

Xaa Trp Xaa Xaa Xaa Xaa Xaa Tyr Xaa Asn Xaa Xaa Phe Xaa Thr Xaa
            195                 200                 205
```

Ser Xaa Thr Phe Ser Tyr Ile Ala Gln Glu
    210             215

<210> SEQ ID NO 30
<211> LENGTH: 215
<212> TYPE: PRT
<213> ORGANISM: Artificial Sequence
<220> FEATURE:
<223> OTHER INFORMATION: Description of Artificial Sequence: Majority
      sequence from the comparison between non-group B
      adenoviral knobs
<221> NAME/KEY: PEPTIDE
<222> LOCATION: (43)
<223> OTHER INFORMATION: Xaa is any amino acid or no amino acid
<221> NAME/KEY: PEPTIDE
<222> LOCATION: (45)..(46)
<223> OTHER INFORMATION: Xaa is any amino acid or no amino acid
<221> NAME/KEY: PEPTIDE
<222> LOCATION: (59)..(76)
<223> OTHER INFORMATION: Xaa is any amino acid or no amino acid
<221> NAME/KEY: PEPTIDE
<222> LOCATION: (78)
<223> OTHER INFORMATION: Xaa is any amino acid or no amino acid
<221> NAME/KEY: PEPTIDE
<222> LOCATION: (97)..(99)
<223> OTHER INFORMATION: Xaa is any amino acid or no amino acid
<221> NAME/KEY: PEPTIDE
<222> LOCATION: (137)
<223> OTHER INFORMATION: Xaa is any amino acid or no amino acid
<221> NAME/KEY: PEPTIDE
<222> LOCATION: (139)..(144)
<223> OTHER INFORMATION: Xaa is any amino acid or no amino acid
<221> NAME/KEY: PEPTIDE
<222> LOCATION: (148)..(149)
<223> OTHER INFORMATION: Xaa is any amino acid or no amino acid
<221> NAME/KEY: PEPTIDE
<222> LOCATION: (173)..(174)
<223> OTHER INFORMATION: Xaa is any amino acid or no amino acid
<221> NAME/KEY: PEPTIDE
<222> LOCATION: (178)..(179)
<223> OTHER INFORMATION: Xaa is any amino acid or no amino acid
<221> NAME/KEY: PEPTIDE
<222> LOCATION: (194)..(195)
<223> OTHER INFORMATION: Xaa is any amino acid or no amino acid

<400> SEQUENCE: 30

Thr Leu Trp Thr Thr Pro Asp Pro Ser Pro Asn Cys Thr Ile Asp Gln
 1               5                  10                  15

Asp Lys Asp Ser Lys Leu Thr Leu Val Leu Thr Lys Cys Gly Ser Gln
            20                  25                  30

Ile Leu Ala Thr Val Ser Leu Ile Val Val Xaa Ala Xaa Xaa Gly Lys
        35                  40                  45

Leu Leu Ile Ile Asn Asn Thr Thr Asn Pro Xaa Xaa Xaa Xaa Xaa Xaa
    50                  55                  60

Xaa Xaa Xaa Xaa Xaa Xaa Xaa Xaa Xaa Xaa Xaa Lys Xaa Phe Thr
65                  70                  75                  80

Ile Lys Leu Leu Phe Asp Ala Asn Gly Val Leu Leu Glu Asn Ser Asn
                85                  90                  95

Xaa Xaa Xaa Leu Gly Lys Ala Tyr Trp Asn Phe Arg Asn Gly Asn Ser
            100                 105                 110

Thr Val Ser Thr Ala Tyr Glu Asn Ala Val Gly Phe Met Pro Asn Leu
        115                 120                 125

Val Ala Tyr Pro Lys Pro Thr Gly Xaa Ser Xaa Xaa Xaa Xaa Xaa
    130                 135                 140

Ala Lys Asp Xaa Xaa Ile Val Tyr Gly Asn Val Tyr Leu Gly Gly Asp
145                 150                 155                 160

Pro Asp Gln Pro Val Val Ile Lys Ile Thr Phe Asn Xaa Xaa Gln Glu

```
                         165                 170                 175
Thr Xaa Xaa Gly Ser Gly Tyr Ser Ile Thr Phe Asp Phe Ser Trp Ser
            180                 185                 190

Lys Xaa Xaa Thr Tyr Ile Asn Val Glu Phe Glu Thr Thr Ser Phe Thr
        195                 200                 205

Phe Ser Tyr Ile Ala Gln Glu
    210                 215
```

<210> SEQ ID NO 31
<211> LENGTH: 248
<212> TYPE: PRT
<213> ORGANISM: Artificial Sequence
<220> FEATURE:
<223> OTHER INFORMATION: Description of Artificial Sequence: Consensus
      sequence from the comparison between non-group B
      adenoviral knobs.
<221> NAME/KEY: PEPTIDE
<222> LOCATION: (6)
<223> OTHER INFORMATION: Xaa is any amino acid or no amino acid
<221> NAME/KEY: PEPTIDE
<222> LOCATION: (9)..(10)
<223> OTHER INFORMATION: Xaa is any amino acid or no amino acid
<221> NAME/KEY: PEPTIDE
<222> LOCATION: (16)..(20)
<223> OTHER INFORMATION: Xaa is any amino acid or no amino acid
<221> NAME/KEY: PEPTIDE
<222> LOCATION: (29)
<223> OTHER INFORMATION: Xaa is any amino acid or no amino acid
<221> NAME/KEY: PEPTIDE
<222> LOCATION: (42)
<223> OTHER INFORMATION: Xaa is any amino acid or no amino acid
<221> NAME/KEY: PEPTIDE
<222> LOCATION: (44)
<223> OTHER INFORMATION: Xaa is any amino acid or no amino acid
<221> NAME/KEY: PEPTIDE
<222> LOCATION: (47)
<223> OTHER INFORMATION: Xaa is any amino acid or no amino acid
<221> NAME/KEY: PEPTIDE
<222> LOCATION: (49)..(51)
<223> OTHER INFORMATION: Xaa is any amino acid or no amino acid
<221> NAME/KEY: PEPTIDE
<222> LOCATION: (53)
<223> OTHER INFORMATION: Xaa is any amino acid or no amino acid
<221> NAME/KEY: PEPTIDE
<222> LOCATION: (55)..(56)
<223> OTHER INFORMATION: Xaa is any amino acid or no amino acid
<221> NAME/KEY: PEPTIDE
<222> LOCATION: (59)
<223> OTHER INFORMATION: Xaa is any amino acid or no amino acid
<221> NAME/KEY: PEPTIDE
<222> LOCATION: (62)..(67)
<223> OTHER INFORMATION: Xaa is any amino acid or no amino acid
<221> NAME/KEY: PEPTIDE
<222> LOCATION: (70)..(71)
<223> OTHER INFORMATION: Xaa is any amino acid or no amino acid
<221> NAME/KEY: PEPTIDE
<222> LOCATION: (74)..(90)
<223> OTHER INFORMATION: Xaa is any amino acid or no amino acid
<221> NAME/KEY: PEPTIDE
<222> LOCATION: (100)..(104)
<223> OTHER INFORMATION: Xaa is any amino acid or no amino acid
<221> NAME/KEY: PEPTIDE
<222> LOCATION: (109)..(111)
<223> OTHER INFORMATION: Xaa is any amino acid or no amino acid
<221> NAME/KEY: PEPTIDE
<222> LOCATION: (117)
<223> OTHER INFORMATION: Xaa is any amino acid or no amino acid
<221> NAME/KEY: PEPTIDE
<222> LOCATION: (120)
<223> OTHER INFORMATION: Xaa is any amino acid or no amino acid
<221> NAME/KEY: PEPTIDE
<222> LOCATION: (128)
<223> OTHER INFORMATION: Xaa is any amino acid or no amino acid
<221> NAME/KEY: PEPTIDE
<222> LOCATION: (142)..(143)

```
<223> OTHER INFORMATION: Xaa is any amino acid or no amino acid
<221> NAME/KEY: PEPTIDE
<222> LOCATION: (147)..(149)
<223> OTHER INFORMATION: Xaa is any amino acid or no amino acid
<221> NAME/KEY: PEPTIDE
<222> LOCATION: (152)..(158)
<223> OTHER INFORMATION: Xaa is any amino acid or no amino acid
<221> NAME/KEY: PEPTIDE
<222> LOCATION: (165)
<223> OTHER INFORMATION: Xaa is any amino acid or no amino acid
<221> NAME/KEY: PEPTIDE
<222> LOCATION: (169)
<223> OTHER INFORMATION: Xaa is any amino acid or no amino acid
<221> NAME/KEY: PEPTIDE
<222> LOCATION: (172)
<223> OTHER INFORMATION: Xaa is any amino acid or no amino acid
<221> NAME/KEY: PEPTIDE
<222> LOCATION: (174)
<223> OTHER INFORMATION: Xaa is any amino acid or no amino acid
<221> NAME/KEY: PEPTIDE
<222> LOCATION: (180)
<223> OTHER INFORMATION: Xaa is any amino acid or no amino acid
<221> NAME/KEY: PEPTIDE
<222> LOCATION: (187)..(189)
<223> OTHER INFORMATION: Xaa is any amino acid or no amino acid
<221> NAME/KEY: PEPTIDE
<222> LOCATION: (191)
<223> OTHER INFORMATION: Xaa is any amino acid or no amino acid
<221> NAME/KEY: PEPTIDE
<222> LOCATION: (193)
<223> OTHER INFORMATION: Xaa is any amino acid or no amino acid
<221> NAME/KEY: PEPTIDE
<222> LOCATION: (195)..(201)
<223> OTHER INFORMATION: Xaa is any amino acid or no amino acid
<221> NAME/KEY: PEPTIDE
<222> LOCATION: (204)..(205)
<223> OTHER INFORMATION: Xaa is any amino acid or no amino acid
<221> NAME/KEY: PEPTIDE
<222> LOCATION: (207)
<223> OTHER INFORMATION: Xaa is any amino acid or no amino acid
<221> NAME/KEY: PEPTIDE
<222> LOCATION: (209)
<223> OTHER INFORMATION: Xaa is any amino acid or no amino acid
<221> NAME/KEY: PEPTIDE
<222> LOCATION: (211)
<223> OTHER INFORMATION: Xaa is any amino acid or no amino acid
<221> NAME/KEY: PEPTIDE
<222> LOCATION: (217)
<223> OTHER INFORMATION: Xaa is any amino acid or no amino acid
<221> NAME/KEY: PEPTIDE
<222> LOCATION: (219)
<223> OTHER INFORMATION: Xaa is any amino acid or no amino acid
<221> NAME/KEY: PEPTIDE
<222> LOCATION: (222)..(223)
<223> OTHER INFORMATION: Xaa is any amino acid or no amino acid
<221> NAME/KEY: PEPTIDE
<222> LOCATION: (226)..(231)
<223> OTHER INFORMATION: Xaa is any amino acid or no amino acid
<221> NAME/KEY: PEPTIDE
<222> LOCATION: (234)
<223> OTHER INFORMATION: Xaa is any amino acid or no amino acid
<221> NAME/KEY: PEPTIDE
<222> LOCATION: (247)
<223> OTHER INFORMATION: Xaa is any amino acid or no amino acid

<400> SEQUENCE: 31

Thr Leu Trp Thr Gly Xaa Asn Pro Xaa Xaa Ala Asn Cys Gln Ile Xaa
  1               5                  10                  15

Xaa Xaa Xaa Xaa Ser Asn Asp Cys Lys Leu Thr Leu Xaa Leu Val Lys
                 20                  25                  30

Asn Gly Gly Leu Val Asn Gly Tyr Val Xaa Leu Xaa Gly Val Xaa Ser
             35                  40                  45

Xaa Xaa Xaa Asn Xaa Leu Xaa Xaa Phe Thr Xaa Lys Asn Xaa Xaa Xaa
 50                  55                  60
```

```
Xaa Xaa Xaa Asn Ile Xaa Xaa Glu Leu Xaa Xaa Xaa Xaa Xaa Xaa
 65              70                  75                  80

Xaa Xaa Xaa Xaa Xaa Xaa Xaa Xaa Xaa Phe Asp Ser Thr Gly Asn
             85                  90                  95

Leu Leu Thr Xaa Xaa Xaa Xaa Leu Ser Ser Leu Xaa Xaa Xaa Lys
            100                 105                 110

Thr Pro Leu Asn Xaa Lys Ser Xaa Gln Asn Met Ala Thr Gly Ala Xaa
            115                 120                 125

Thr Xaa Ala Lys Gly Phe Met Pro Ser Thr Thr Ala Tyr Xaa Xaa Pro
        130                 135                 140

Phe Asn Xaa Xaa Xaa Arg Glu Xaa Xaa Xaa Xaa Xaa Xaa Xaa Glu Asn
145                 150                 155                 160

Tyr Ile Tyr Gly Xaa Cys Tyr Tyr Xaa Ala Ser Xaa Asp Xaa Thr Leu
                165                 170                 175

Phe Pro Leu Xaa Ile Ser Val Met Leu Asn Xaa Xaa Xaa Arg Xaa Ile
            180                 185                 190

Xaa Ser Xaa Xaa Xaa Xaa Xaa Xaa Thr Ser Xaa Xaa Tyr Xaa Ile
            195                 200                 205

Xaa Phe Xaa Trp Ser Leu Asn Ala Xaa Gly Xaa Ala Pro Xaa Xaa Glu
210                 215                 220

Thr Xaa Xaa Xaa Xaa Xaa Xaa Thr Leu Xaa Thr Ser Pro Phe Thr Phe
225                 230                 235                 240

Ser Tyr Ile Arg Glu Asp Xaa Asp
                245
```

<210> SEQ ID NO 32
<211> LENGTH: 248
<212> TYPE: PRT
<213> ORGANISM: Artificial Sequence
<220> FEATURE:
<223> OTHER INFORMATION: Description of Artificial Sequence: Majority
      sequence from the comparison between non-group B
      adenoviral knobs.
<221> NAME/KEY: PEPTIDE
<222> LOCATION: (9)
<223> OTHER INFORMATION: Xaa is any amino acid or no amino acid
<221> NAME/KEY: PEPTIDE
<222> LOCATION: (47)
<223> OTHER INFORMATION: Xaa is any amino acid or no amino acid
<221> NAME/KEY: PEPTIDE
<222> LOCATION: (55)..(56)
<223> OTHER INFORMATION: Xaa is any amino acid or no amino acid
<221> NAME/KEY: PEPTIDE
<222> LOCATION: (62)..(66)
<223> OTHER INFORMATION: Xaa is any amino acid or no amino acid
<221> NAME/KEY: PEPTIDE
<222> LOCATION: (74)..(89)
<223> OTHER INFORMATION: Xaa is any amino acid or no amino acid
<221> NAME/KEY: PEPTIDE
<222> LOCATION: (100)..(103)
<223> OTHER INFORMATION: Xaa is any amino acid or no amino acid
<221> NAME/KEY: PEPTIDE
<222> LOCATION: (109)..(111)
<223> OTHER INFORMATION: Xaa is any amino acid or no amino acid
<221> NAME/KEY: PEPTIDE
<222> LOCATION: (142)..(143)
<223> OTHER INFORMATION: Xaa is any amino acid or no amino acid
<221> NAME/KEY: PEPTIDE
<222> LOCATION: (152)..(157)
<223> OTHER INFORMATION: Xaa is any amino acid or no amino acid
<221> NAME/KEY: PEPTIDE
<222> LOCATION: (172)
<223> OTHER INFORMATION: Xaa is any amino acid or no amino acid
<221> NAME/KEY: PEPTIDE
<222> LOCATION: (187)..(188)
<223> OTHER INFORMATION: Xaa is any amino acid or no amino acid
<221> NAME/KEY: PEPTIDE -continued

```
<222> LOCATION: (196)..(201)
<223> OTHER INFORMATION: Xaa is any amino acid or no amino acid
<221> NAME/KEY: PEPTIDE
<222> LOCATION: (204)..(205)
<223> OTHER INFORMATION: Xaa is any amino acid or no amino acid
<221> NAME/KEY: PEPTIDE
<222> LOCATION: (217)
<223> OTHER INFORMATION: Xaa is any amino acid or no amino acid
<221> NAME/KEY: PEPTIDE
<222> LOCATION: (222)..(223)
<223> OTHER INFORMATION: Xaa is any amino acid or no amino acid
<221> NAME/KEY: PEPTIDE
<222> LOCATION: (227)..(229)
<223> OTHER INFORMATION: Xaa is any amino acid or no amino acid
<221> NAME/KEY: PEPTIDE
<222> LOCATION: (247)
<223> OTHER INFORMATION: Xaa is any amino acid or no amino acid

<400> SEQUENCE: 32

Thr Leu Trp Thr Gly Ile Asn Pro Xaa Glu Ala Asn Cys Gln Ile Met
 1               5                  10                  15

Glu Ser Ser Glu Ser Asn Asp Cys Lys Leu Thr Leu Val Leu Val Lys
                20                  25                  30

Asn Gly Gly Leu Val Asn Gly Tyr Val Tyr Leu Ile Gly Val Xaa Ser
            35                  40                  45

Asp Thr Val Asn Met Leu Xaa Xaa Phe Thr Asn Lys Asn Xaa Xaa Xaa
    50                  55                  60

Xaa Xaa Ile Asn Ile Thr Ala Glu Leu Xaa Xaa Xaa Xaa Xaa Xaa Xaa
65                  70                  75                  80

Xaa Xaa Xaa Xaa Xaa Xaa Xaa Xaa Phe Phe Asp Ser Thr Gly Asn
                85                  90                  95

Leu Leu Thr Xaa Xaa Xaa Xaa Ser Leu Ser Ser Leu Xaa Xaa Xaa Lys
                100                 105                 110

Thr Pro Leu Asn His Lys Ser Gly Gln Asn Met Ala Thr Gly Ala Ile
            115                 120                 125

Thr Ser Ala Lys Gly Phe Met Pro Ser Thr Thr Ala Tyr Xaa Xaa Pro
    130                 135                 140

Phe Asn Thr Asn Ser Arg Glu Xaa Xaa Xaa Xaa Xaa Lys Glu Asn
145                 150                 155                 160

Tyr Ile Tyr Gly Thr Cys Tyr Tyr Thr Ala Ser Xaa Asp His Thr Leu
                165                 170                 175

Phe Pro Leu Asp Ile Ser Val Met Leu Asn Xaa Xaa Ser Arg Ala Ile
            180                 185                 190

Ser Ser Glu Xaa Xaa Xaa Xaa Xaa Xaa Thr Ser Xaa Xaa Tyr Ala Ile
        195                 200                 205

Arg Phe Thr Trp Ser Leu Asn Ala Xaa Gly Glu Ala Pro Xaa Xaa Glu
    210                 215                 220

Thr Ser Xaa Xaa Xaa Ala Ala Thr Leu Val Thr Ser Pro Phe Thr Phe
225                 230                 235                 240

Ser Tyr Ile Arg Glu Asp Xaa Asp
                245
```